(12) United States Patent
Puppels et al.

(10) Patent No.: US 10,531,818 B2
(45) Date of Patent: Jan. 14, 2020

(54) TISSUE SAMPLE ANALYSIS

(71) Applicant: Erasmus University Medical Center Rotterdam, Rotterdam (NL)

(72) Inventors: Gerwin Jan Puppels, Schiedam (NL);
Elisa Maria Barroso, Rotterdam (NL);
Tom Christian Bakker Schut, Zoetermeer (NL); Roeland W. H. Smits, Rhoon (NL); Peter Jacobus Caspers, Capelle aan den IJssel (NL);
Senada Koljenovic, Rotterdam (NL)

(73) Assignee: ERASMUS UNIVERSITY MEDICAL CENTER ROTTERDAM, Rotterdam (NL)

( * ) Notice: Subject to any disclaimer, the term of this patent is extended or adjusted under 35 U.S.C. 154(b) by 0 days.

(21) Appl. No.: 16/069,773

(22) PCT Filed: Jan. 18, 2016

(86) PCT No.: PCT/NL2016/050041
§ 371 (c)(1),
(2) Date: Jul. 12, 2018

(87) PCT Pub. No.: WO2017/126955
PCT Pub. Date: Jul. 27, 2017

(65) Prior Publication Data
US 2018/0317818 A1    Nov. 8, 2018

(51) Int. Cl.
*G01J 3/28* (2006.01)
*A61B 5/1455* (2006.01)
(Continued)

(52) U.S. Cl.
CPC .......... *A61B 5/1455* (2013.01); *A61B 5/0075* (2013.01); *G01N 21/4795* (2013.01); *G01N 21/65* (2013.01)

(58) Field of Classification Search
CPC .... G01J 3/02; G01J 3/28; G01J 3/2803; G01J 3/10; G01J 3/2823
(Continued)

(56) References Cited

U.S. PATENT DOCUMENTS 6,526,298 B1 * 2/2003 Khalil ................. A61B 5/0059
600/310
2006/0276696 A1   12/2006 Schurman
(Continued)

FOREIGN PATENT DOCUMENTS

CN       103315749 B    1/2015
EP       1 567 852      6/2007
(Continued)

OTHER PUBLICATIONS

Caspers et al. (2001) J. Invest. Dermatol. 116(3):434-442 "In Vivo Concoal Raman Microspectroscopy of the Skin: Noninvasive Determination of Molecular Concentration Profiles".
(Continued)

*Primary Examiner* — Md M Rahman
(74) *Attorney, Agent, or Firm* — Adsero IP

(57) ABSTRACT

Method and instrument for analysing a tissue sample. Localized concentrations of an analyte are measured at a plurality of spaced apart locations around a controlled depth. Spatial variance of the analyte is calculated based on the measured analyte concentrations. The procedure is repeated while varying the controlled depth to obtain the spatial variance as a function of depth. Tissue at a particular depth may be evaluated as tumour tissue when the spatial variance is below the threshold. For example, a section distance is calculated between the tissue surface and a depth where the measured spatial variance crosses a predetermined threshold
(Continued)

variance. Feedback can be provided based on a comparison between a calculated section distance and a pre-set minimum section margin.

14 Claims, 14 Drawing Sheets

(51) Int. Cl.
*G01N 21/47* (2006.01)
*G01N 21/65* (2006.01)
*A61B 5/00* (2006.01)

(58) Field of Classification Search
USPC .......................................................... 356/326
See application file for complete search history.

(56) References Cited

U.S. PATENT DOCUMENTS

| | | | |
|---|---|---|---|
| 2008/0039742 A1 | 2/2008 | Hashimshony | |
| 2009/0116032 A1 | 5/2009 | Zara | |
| 2010/0241100 A1* | 9/2010 | Blumenfeld | A61B 5/0075 604/503 |
| 2014/0023255 A1* | 1/2014 | Lim | G06T 11/005 382/131 |
| 2014/0046152 A1 | 2/2014 | Bechtel | |
| 2014/0180133 A1* | 6/2014 | Brennan | A61B 1/00096 600/478 |
| 2015/0109617 A1* | 4/2015 | Gilbert | A61B 5/14532 356/300 |
| 2016/0249836 A1* | 9/2016 | Gulati | A61B 5/1455 600/316 |
| 2016/0290926 A1* | 10/2016 | Notingher | G01N 33/4833 |
| 2017/0322084 A1* | 11/2017 | Haider | A61B 5/14532 |

FOREIGN PATENT DOCUMENTS

| | | |
|---|---|---|
| WO | WO 02/082990 | 10/2002 |
| WO | WO 2008/057578 | 5/2008 |
| WO | WO 2008/058014 | 5/2008 |
| WO | WO 2009/002170 | 12/2008 |
| WO | WO 2009/111542 | 9/2009 |
| WO | WO 2014/162289 | 10/2014 |
| WO | WO 2015/183994 | 12/2015 |

OTHER PUBLICATIONS

International Search Report from PCT/NL2016/050041 dated Oct. 10, 2016.
Jacob and Carson (2014) BMC Medical Imaging 14:1-11; http://www.biomedcentral.com/1471-2342/14/1 "Automated measurement of heterogeneity in CT images of healthy and diseased rat lungs using varigram analysis of an octree decomposition".
Kennedy et al. (2013) Journal of Biomedical Optics 18(12):121510-1-121510-8 (Downloaded from: http://biomedicaloptics.spiedigitallibrary.org on Aug. 17, 2015) "Needle optical coherence elastography for the measurement of microscale mechanical contrast deep with human breast tissues".
Saager et al. (2011) Journal of Biomedical Optics 16(12):126013-1-126013-5 "Quantitative fluorescence imaging of protoporphyrin IX through determination of tissue optical properties in the spatial frequency domain".
Tearney et al, (2006) Society for Photo-Optical Instrumentation Engineers pp. 1-21. Also, published in final edited form as: Journal of Biomedical Optics 11(2): 021002. doi: 10.1117/1.2192697 "Optical coherence tomography for imaging the vulnerable plaque".
Wolthuis et al. (2001) J. Anal. Chem. 73:3915-3920 "Determination of Water Concentration in Brain Tissue by Raman Spectroscopy".

* cited by examiner

TISSUE SAMPLE ANALYSIS

RELATED APPLICATIONS

This application is a 35 U.S.C. § 371 national phase application of PCT/NL2016/050041 (WO 2017/126955), filed on Jan. 18, 2016, entitled "Tissue Sample Analysis", which is incorporated herein by reference in its entirety.

TECHNICAL FIELD AND BACKGROUND

The present disclosure relates to a method of analysing tissue samples. The disclosure also relates to an instrument for analysing tissue samples and a computer readable medium for causing the instrument to perform analysis of tissue samples.

Some aspects of the present disclosure may improve intra-operative inspection of resection margins on a tumour resection specimen, to assess if adequate margins have been achieved. For example, oral cavity cancer is a major public health issue. Most oral cancers arise from the epithelium of the mucosal surfaces and are referred to as oral cavity squamous cell carcinoma (OCSCC). Mortality from OCSCC is high. Despite advances in treatment modalities (surgery, radiotherapy, chemotherapy), mortality has not shown significant improvement over the last decades.

Surgery is the mainstay of treatment for OCSCC. Complete cure may be accomplished by adequate surgery. Adequate tumour resection with acceptable remaining function and appearance is the main goal. For example, resection margins (defined as the smallest distance between tumour and resection surface) can be histopathologically classified as clear: >5 mm, close: 1 to 5 mm, and positive: <1 mm. Clear margins are regarded as adequate, close and positive margins as inadequate. In OCSCC, as in many other tumours, adequate tumour resection is often hard to achieve. The common causes are lack of reliable guidance of the surgeon and proximity of relevant structures in the operating field.

Patients with inadequate resection margins receive postoperative adjuvant treatment (chemotherapy and/or radiation), or re-operation. However, such treatments can significantly add to the morbidity of surgery while their efficacy is questioned. For the oral cavity, with its complex anatomy, visual inspection and palpation by the surgeon, are insufficient to warrant adequate resections. More information is needed to guide the surgeon.

Intraoperative assessment of resection margins on the resected tissue (referred to as "specimen driven") is considered to be superior to assessment from the wound bed (referred to as "defect driven"), leading to a higher surgical success rate, lower local tumour recurrence, and increased patient survival. Guidance of surgery by intraoperative "specimen driven" assessment of resection margins is recommended. The procedure may greatly benefit from intra-operative histological assessment of resection margins for example by means of the so-called frozen section procedure. In the frozen section procedure the surgeon takes tissue samples from the surgical wound bed for microscopic evaluation by a pathologist. However, the procedure is laborious and time consuming and therefore limited to inspection of only a small number samples and fraught with sampling error. Inadequate margins are easily missed in the frozen section procedure, especially when the surgical wound is sampled.

There is a desire to provide methods and instruments which may improve accuracy of tissue sample analysis, in particular to better distinguish tumour and healthy tissue.

SUMMARY

One aspect of the present disclosure provides a method of analysing a tissue sample. The method comprises measuring a localized concentration of an analyte at a plurality of spaced apart locations around a controlled depth below a surface of the tissue sample. The method further comprises calculating a spatial variance of the concentration of the analyte at the controlled depth. The procedure of measuring concentrations and calculating the spatial variance thereof may be repeated for different depths. In this way the spatial variance of the analyte can be calculated as a function of depth.

The inventors find that the degree of spatial variance of analyte concentrations in a resected tissue may be correlated with the presence or absence of a tumour. For example, analyte concentrations in tumour tissue may show less variation than in normal tissue. Without being bound by theory it is noted that tumour tissue typically exhibits a relatively high degree of homogeneity compared to normal healthy tissue. For example, the tumour mainly comprises very similar or the essentially the same cell structures and analyte concentrations.

By measuring spatial variances for a plurality of controlled depths, the spatial variance can be determined as a function of depth. For example, the spatial variance for each depth is calculated using at least two different measurements, preferably between three and ten different measurements, e.g. five, six, or seven measurements at closely spaced locations. By providing the measurement locations relatively close together, the accuracy of the measurement as a function of depth may be improved. On the other hand, the distance between measurements should be large enough to sample a sufficient region to determine the analyte variance. For example, the measurement locations are closely spaced at a distance between ten and five hundred micrometres, preferably between fifty and two hundred micrometres, e.g. a distance between measurement locations is at least one hundred micrometres. Measurement regions may partly overlap but should not fully overlap to measure different locations and concentrations.

By calculating a section distance between the tissue surface and a depth below the tissue surface where the measured spatial variance crosses a predetermined threshold variance, it can be estimated how deep the tumour tissue is located below the surface of the resected specimen. For example, an evaluation parameter is calculated based on a threshold for the spatial variance of the concentration of the analyte. For example, tissue at a particular depth can be evaluated as tumour tissue when the spatial variance is below the threshold. By providing a feedback signal based on a comparison between the calculated section distance and a pre-set minimum section margin, an operator may be alerted to the fact that the tumour tissue was cut with insufficient margin. For example, it may be determined that the tissue sample is inadequately resected when the section distance is lower than the minimum section margin. This may prompt further action.

By alternatively or additionally calculating a mean concentration of the analyte as a function of the depth, further distinction can be made between different types of tissue. By calculating a section distance between the tissue surface and a depth below the tissue surface where either one or both the measured mean concentration or spatial variance crosses a respective or combined predetermined threshold, estimation of the tumour border may be more accurate.

A plurality of locations for calculation of the spatial variance that are spaced apart along a depth direction can be measured for example by scanning the concentration while probing at different depths below the tissue surface. For example, the spatial variance is calculated as a standard deviation of multiple measurements taken over a predetermined depth margin around a depth below the tissue surface. Alternatively, or in addition, a plurality of locations for calculation of the spatial variance may be spaced apart along a lateral direction transverse to a coordinate of the controlled depth. For example, the spatial variance is calculated as a standard deviation of multiple measurements taken in a lateral region at a depth below the tissue surface. Also combinations are possible, e.g. wherein the spatial variance measure with points that are spaced apart both in the depth and lateral directions.

Analyte concentration can be measured using various techniques. Optical techniques are preferable to accurately measure local concentrations, i.e. within a specific bounded region. In particular, Raman spectroscopy is found to be both accurate and relatively easy to use for measuring and distinguishing concentrations of water and other biologically relevant analytes. For example, a concentration of a water analyte can be calculated from a spectral response of the tissue sample by comparing an amplitude of the responses from the water with responses from other molecules. By making a comparative measurement between spectral amplitudes associated with different molecules, accuracy may be improved. For example, the concentration of an analyte can be determined from an optical response of the tissue sample measured as a function of a depth below the tissue surface.

By measuring the spectral response using a needle comprising an optical waveguide, a light spot can be accurately positioned inside the tissue. For example, the probe light is transmitted via the optical waveguide through the needle at a controlled variable depth of the needle into the tissue surface and an optical response of the tissue sample So the probe light is measured for calculating the concentration of the analyte at the controlled variable depth. Preferably, the optical waveguide comprises an optical fibre inside the needle. For example, the optical fibre is fixated inside the needle e.g. using epoxy resin. By cutting the optical fibre at an angle flush with an angle of the needle, light can be brought all the way to the tip of the needle. The measurement region for each measurement is preferably small, e.g. less than a millimetre in diameter, or even less than half a millimetre. For example, the optical waveguide and/or needle may comprise a lens to focus light to a relatively small region in the tissue.

Instead of a single fibre, it is also possible to provide a bundle of two three, or more fibres inside the needle. By having adjacent optical fibres individual measurements of the concentration of analyte may be provided at spaced apart locations in the tissue sample, e.g. with lateral spacing there between. Alternatively, or in addition, by providing the optical waveguide with a lens inside the needle, light from a fibre bundle can be imaged at spaced apart locations in the tissue sample. For example, a gradient index lens can be used advantageously inside with a needle. By providing a first gradient index lens fixated inside the needle and a second gradient index lens connected to a fibre bundle, the needle can be disposable. For example, the second gradient index lens is connectable to a disposable needle which comprises the first gradient index lens. For example two half-period gradient index lenses can be used that together image the fibre bundle inside the tissue.

Alternative to a needle, measuring may also be performed using other means. For example, a non-invasive confocal optical system may be used, in particular for relatively shallow depths below the tissue surface. For example, probe light is transmitted at a controlled variable depth into the tissue surface by varying a distance of a focal point of probe light below the tissue surface and an optical response of the tissue sample So the probe light is measured for calculating the concentration of the analyte at the controlled variable depth. For example, the distance of the focal point is varied by a moveable lens or other means.

For some types of tumour, e.g. oral cavity squamous cell carcinoma (OCSCC), it is found that the water concentration and variation can provide an accurate indicator for the presence or absence of tumour tissue. For example, a threshold variance is set at a value between five and twenty-five percent below which for example, a tissue is classified as tumour tissue when the standard deviation of a number of water concentration measurements, e.g. measured over a measuring distance of one millimeter in the tissue, is less than fifteen percent. For example, a threshold mean is set at a value between sixty and ninety percent, for example a tissue is classified as tumour tissue when the mean value of a number of water concentration measurements, e.g. measured over a measuring distance of one millimeter in the tissue, is more than seventy percent. Also combinations are possible. For example, a threshold ratio is set at a value between two and twenty, for example a tissue is classified as tumour tissue when the ratio of the mean over the variance of a number of water concentration measurements, e.g. measured over a measuring distance of one millimeter in the tissue, is more than four and half.

Another or further aspect of the present disclosure provides an instrument for analysing a tissue sample. The instrument may comprise a probe configured to measure a localized concentration of an analyte at a plurality of spaced apart locations around a controlled depth below a surface of the tissue sample. The instrument may further comprise or couple to a controller configured to calculate a spatial variance of the concentration of the analyte as a function of the controlled depth.

The probe may be an optical probe which may e.g. be connected to an interrogator device via appropriate cabling which may include optical and electrical wiring. In a preferred embodiment, the probe comprises a needle having a needle tip formed to penetrate a tissue surface and an optical waveguide arranged to transmit light through the needle. Optionally, the probe comprises a probe housing for holding the needle and at least one of an actuator or a sensor configured to receive or generate a depth signal to determine a depth position of the needle tip relative to the tissue surface. Also other types of probes can be envisioned, optical or otherwise.

The optical probe may allow to quickly measure e.g. the Raman spectrum at a variable controlled depth in a tissue specimen. By measuring the concentration as a function of depth the margin of healthy tissue surrounding the tumour tissue can be determined to see if sufficient margin around the tumour has been cut out. By using an optical fiber as waveguide inside a needle, light can be effectively transmitted to a specific controlled depth of the tissue sample. Depending on the tissue properties, a specific response spectrum can be measured by collecting the light through the same or a further optical fiber. The optical fiber may extend beyond a length of the needle to connect to an optical interrogator device. Preferably, the fiber and instrument are adapted for measuring a Raman spectrum. Accordingly, the fiber material can be particularly adapted to transmit the corresponding wavelengths. For example, the optical fiber comprises a core, a cladding and optionally a coating for transmitting light at least in a wavelength range between 600 to 1000 nanometres. Also other wavelength ranges may be used.

The depth measurement of the needle may be based e.g. on a measured displacement of the needle with respect to a reference plane. By providing the probe housing with a tissue engaging surface, the tissue surface can be determined by physical interaction with the probe. By guiding the needle transverse to the tissue engaging surface, the depth of the needle tip in the tissue may be determined by measuring and/or actuating the displacement of the needle with respect to the tissue engaging surface. For example, the needle may slide through a linear guidance. By allowing the needle to fully retract into the housing, the instrument may be more safe to handle. When the housing is brought in contact with a tissue, the needle may extend from the housing into the tissue.

By providing an actuator, movement of the needle during the measurement can be well controlled. For example, the probe may receive a depth signal as input to the actuator to provide an absolute or relative position of the needle tip with respect to the tissue surface and/or the tissue engaging surface. For example, the actuator may comprise a translation stage with a moveable stage attached to the needle and/or a needle mount. The probe housing may comprise the appropriate, e.g. electrical, wiring to transfer the depth signal to the actuator to control actuation of the depth position of the needle.

By providing a distance sensor alternative or in addition to an actuator, the depth position of the needle tip may be measured. For example, the depth signal may be calculated from an output of the sensor. For example, the sensor may measure a translation of the needle relative to the tissue engaging surface and/or the tissue surface. When the tissue engaging surface is moveable with respect to the needle, the sensor may measure a translation of the tissue engaging surface. Also other types of sensors may be used, e.g. to measure a distance between a front of the probe housing and the tissue surface using a needle that is stationary with respect to the housing.

By alternatively or additionally providing a pressure sensor, a contact of the probe housing and/or the needle with the tissue surface can be detected. For example, a first pressure signal of contact between the probe housing and tissue may cause actuation of the needle.

By providing the instrument with a z-actuator to control the depth of the needle with respect tot the tissue surface, automatic measurement at different depths can be performed. By providing an xy-actuator to scan a tissue surface, spectral measurements at different locations can be automatically performed.

By providing the instrument with a display screen various measurements may be displayed. By using a digital camera, a picture of the tissue sample can be shown. By generating an image wherein the picture of the tissue sample is overlaid with one or more indicators of tissue measurements performed by the optical probe, the user may gain additional insight. For example, positions of the indicators in the image may correlate with positions of measurements on the tissue sample. For example, different indicators may be shown as a function of the depth dependent spectral measurement for each location. For example, a picture of the tissue engaging surface may be overlaid with visual indicators of the spectral signatures as a function of position on the tissue. When the visual indicators are generated as a function of a margin of healthy tissue surrounding the tumour tissue, the user may relocate portions of the section tissue where the tumour was optimally removed.

The interrogator is preferably equipped with a light source to provide the input light signal into the optical waveguide for probing inside the tissue sample. The interrogator is preferably equipped with a light sensor to receive a response light signal from the optical waveguide indicative of a response of the tissue sample So the input light signal. To measure a spectral signature, a dispersion or diffraction element may be provided to spectrally resolve the response light signal on the light sensor. A depth control circuit may be used to determine the depth signal and calculate the depth position of the needle tip with respect to the tissue surface. Of course the circuit may be built from suitable hardware and/or software components. Also other circuitry and/or program instructions may be present. For example, an analyser may be configured to determine a plurality of spectral signatures of the tissue sample as a function of the depth position in the tissue sample based on the response light signal as a function of the depth signal. These and other components may be under control of a processor, e.g. controller configured to coordinate a depth of the needle, wherein the controller stores the spectral signature as a function of depth. For example, the controller is configured to store a series of spectral measurements as a function of depth.

A further aspect of the present disclosure provides a computer readable medium with software instructions that when executed by an instrument as described herein cause execution of one or more of the methods as described herein, in particular automated measurement of a tissue sample.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1A:
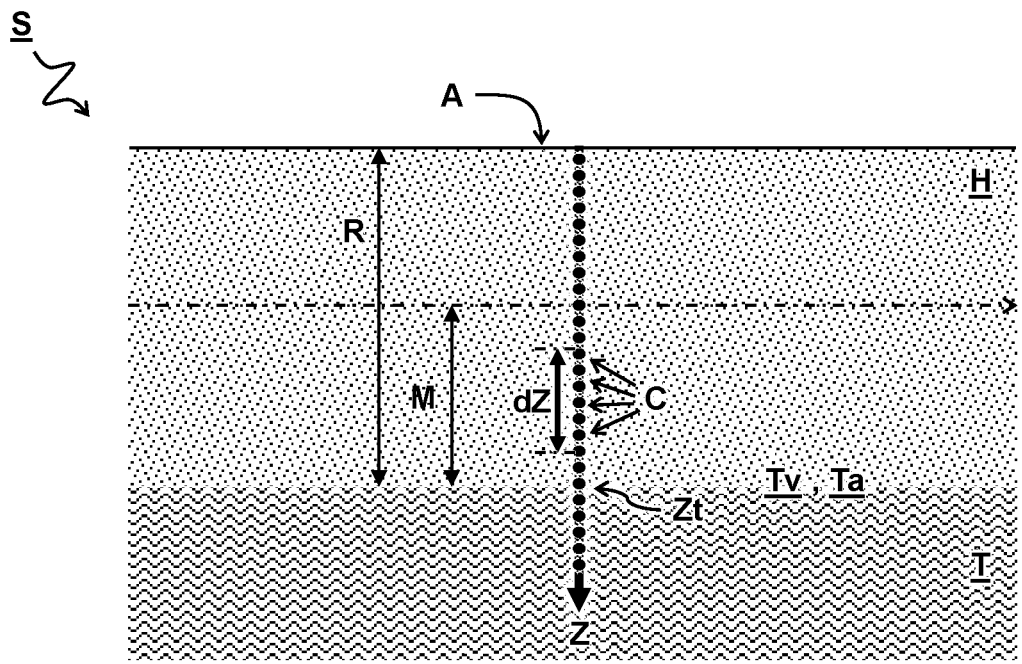
FIGS. 1A and 1B schematically illustrate a first embodiment of a method of measuring a tissue sample.

In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise. All publications, patent applications, patents, and other references mentioned herein are incorporated by reference in their entirety. In case of conflict, the present specification, including definitions, will control.

Analyte concentrations can be measured in different ways. For example optical measuring techniques may provide a spectral signature that can be related to a measure of the analyte concentration. In general, any method to determine a measure of the localized analyte concentration, i.e. at a specific region of the tissue, may be suitable. For example, an absolute concentration of an analyte may be measured and/or a concentration of one analyte may be measured relative to the concentration of one or more other analytes.

Spatial variance of the analyte can also be calculated in different ways, e.g. based on two or more measured analyte concentrations. In general the spatial variance may provide a measure of the amount of variation of the analyte concentration, e.g. at closely spaced but distinct locations in the tissue. For example, the standard deviation of a number of measurements can be used to determine the analyte variance. Alternatively, or in addition, a concentration difference between two or more measurements may provide a measure of the variance. Also other types of calculations may be used to yield a measure of the variation of the analyte concentration.

For example, water content is found to be a possible discriminator between tumour and healthy tissue. Nuclear MRI can show that the main cause of the differences observed between the relaxation times of normal and malignant tissues is the higher water content in the latter. The present disclosure takes the analysis further by alternatively or additionally measuring the spatial variance of the water concentration. The inventors find in particular that while the mean water concentration in tumour tissue is typically higher than in healthy tissue, the spatial variance of the water concentration is typically lower. In other words, tumour tissue tends to have a less variable water concentration than healthy tissue, which can be used to discriminate there between.

The present disclosure investigates for example the possibility of using Raman spectroscopy for intraoperative assessment of surgical margins by ex vivo inspection of the resection specimen. Raman spectroscopy is a non-destructive optical technique that requires no sample preparation. It can provide real-time information about the molecular composition of tissue. This enables tissue characterization based on quantitative molecular information. Raman spectroscopy is very suitable for rapid quantitative determination of the water concentration of tissue.

For example, water concentration can be measured in the so-called high wavenumber (HWVN) part of the Raman spectrum, which dominated by the CH-, OH-, and NH-stretching vibrations. This spectral region is very suitable for the use of optical fibers, because no background signal is generated in the optical fiber materials, which allows for simple inexpensive probe designs (even as simple as a single optical fiber which guides laser light to the tissue and guides Raman scattered light from the tissue back to the spectrometer. Such probes can be fitted in thin hypodermic needle to access deeper layers of tissue.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The description of the exemplary embodiments is intended to be read in connection with the accompanying drawings, which are to be considered part of the entire written description. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

FIG. 1A illustrates an embodiment of a resected tissue sample S wherein measurements are taken of a localized concentration of an analyte C at a plurality of spaced apart locations dZ around a controlled variable depth Z below a surface A of the tissue sample S.

Figure 1B:
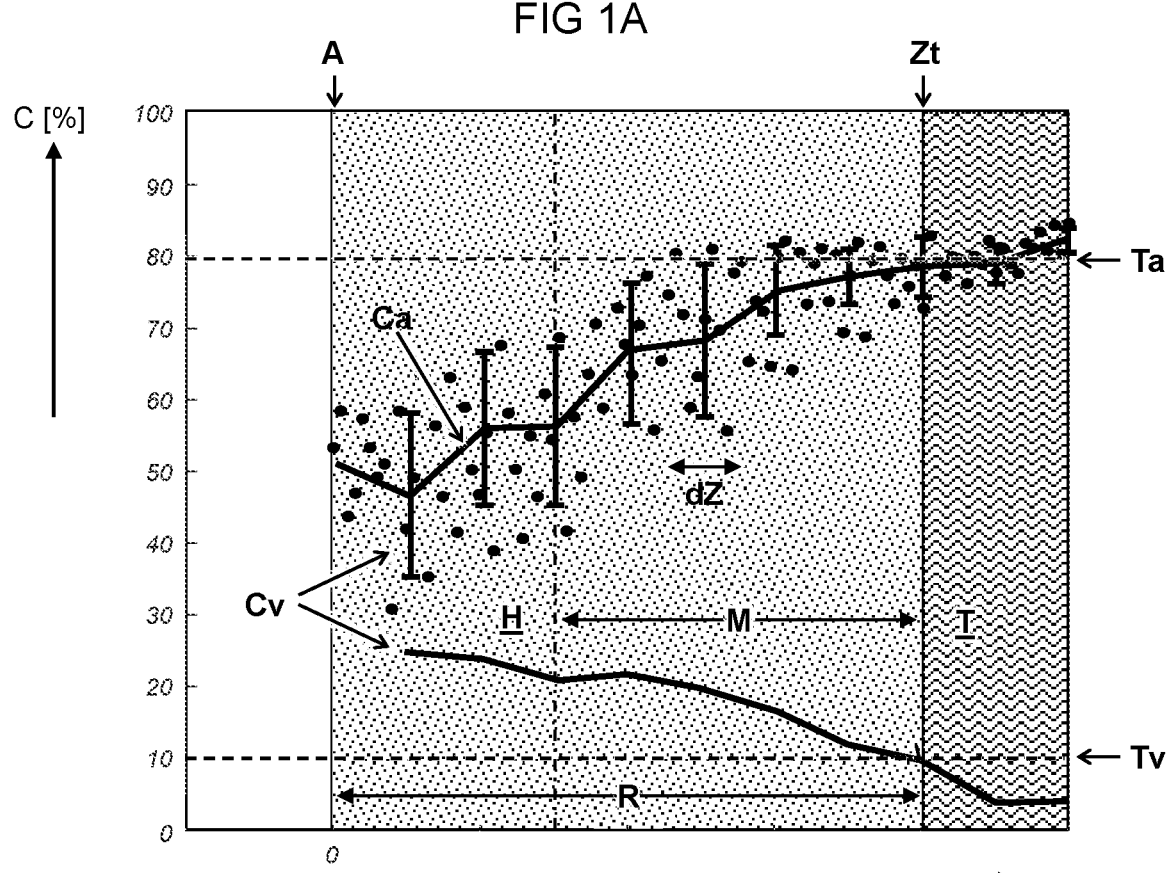

FIG. 1B illustrates a corresponding typical model graph of the concentration of the analyte C as a function of depth Z. For example, each of the black dots may correspond to a localized concentration of the analyte.

One embodiment for analysing a resected tissue sample S comprises a procedure of measuring localized concentrations of an analyte C at a plurality of spaced apart locations dX,dZ around a controlled depth Z below a surface A of the tissue sample S. In another or further embodiment, the procedure comprises calculating a spatial variance Cv of the analyte C based on the plurality measured concentrations around the controlled depth Z. The procedure may be repeated or continued while varying the controlled depth Z to obtain the spatial variance Cv as a function of the controlled depth Z. For example, spatial variances Cv are calculated for a plurality of controlled depths Z.

In one embodiment, the spatial variance Cv for each depth is calculated using at least two different measurements, preferably more, e.g. between three and ten different measurements at closely spaced locations. More measurements can provide greater reproducibility but may also take more time. Preferably, the locations are relatively closely spaced, e.g. within a distance of one millimetre. On the other hand, the locations are preferably spaced apart enough to make distinct measurements, e.g. a distance between measurement locations is at least one hundred micrometres.

In one embodiment, the method comprises calculating a section distance R between the tissue surface A and a depth below the tissue surface A where the measured spatial variance Cv crosses a predetermined threshold variance Tv. In another or further embodiment, the method comprises calculating a mean concentration Ca of the analyte C as a function of the depth Z; and calculating a section distance R between the tissue surface A and a depth below the tissue surface A where either one or both the measured mean concentration Ca or spatial variance Cv crosses a respective or combined predetermined threshold Tv,Tc. A combined threshold may e.g. comprise a ratio of the mean concentration Ca and spatial variance Cv. Also other function of Ca and Cv may be used with corresponding thresholds.

In one embodiment, an evaluation parameter is calculated based on a threshold for the spatial variance Cv of the concentration of the analyte, wherein tissue at a particular depth is evaluated as tumour tissue T when the spatial variance Cv is below the threshold. For example, it may be determined that the tissue sample is inadequately resected when the section distance R is lower than the minimum section margin M.

In the embodiment of FIG. 1, the plurality of locations for calculation of the spatial variance Cv are spaced apart along a depth direction dZ. For example, the spatial variance Cv is calculated as a standard deviation of multiple measurements taken over a predetermined depth margin dZ around a depth Z below the tissue surface A.

Figure 2A:
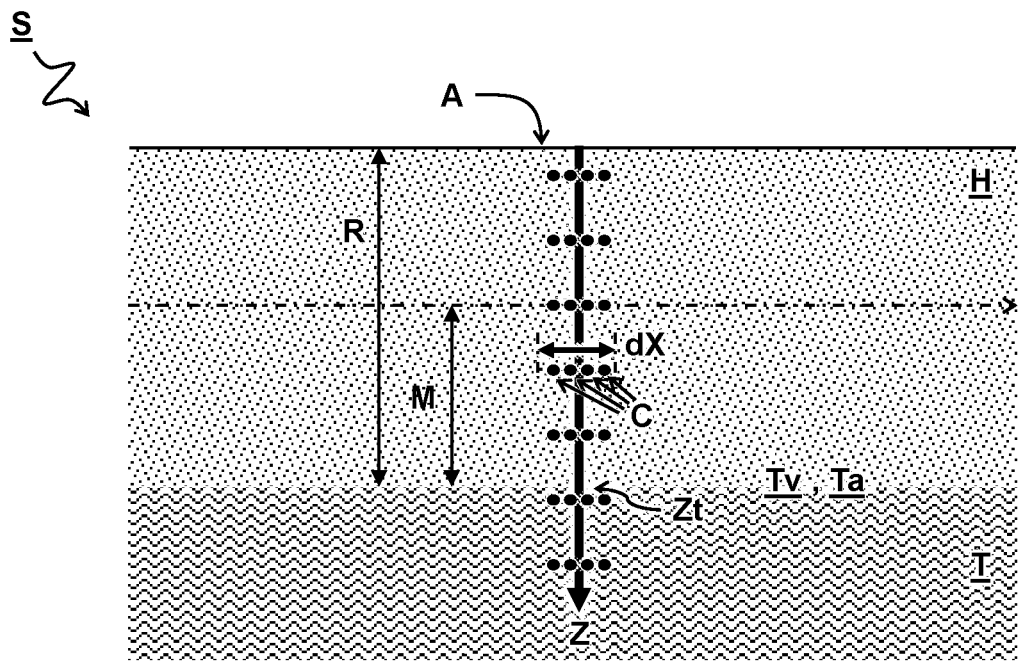
FIGS. 2A and 2B schematically illustrate a second embodiment of a method of measuring a tissue sample.

FIG. 2 is similar to FIG. 1, except in this case the plurality of locations for calculation of the spatial variance Cv are spaced apart along a lateral direction dX transverse to a coordinate of the controlled depth Z. For example, the spatial variance Cv is calculated as a standard deviation of multiple measurements taken in a lateral region dX at a depth Z below the tissue surface A. Of course also combinations are possible, e.g. wherein concentration variance is determined both in the depth and lateral directions.

Figure 3A:
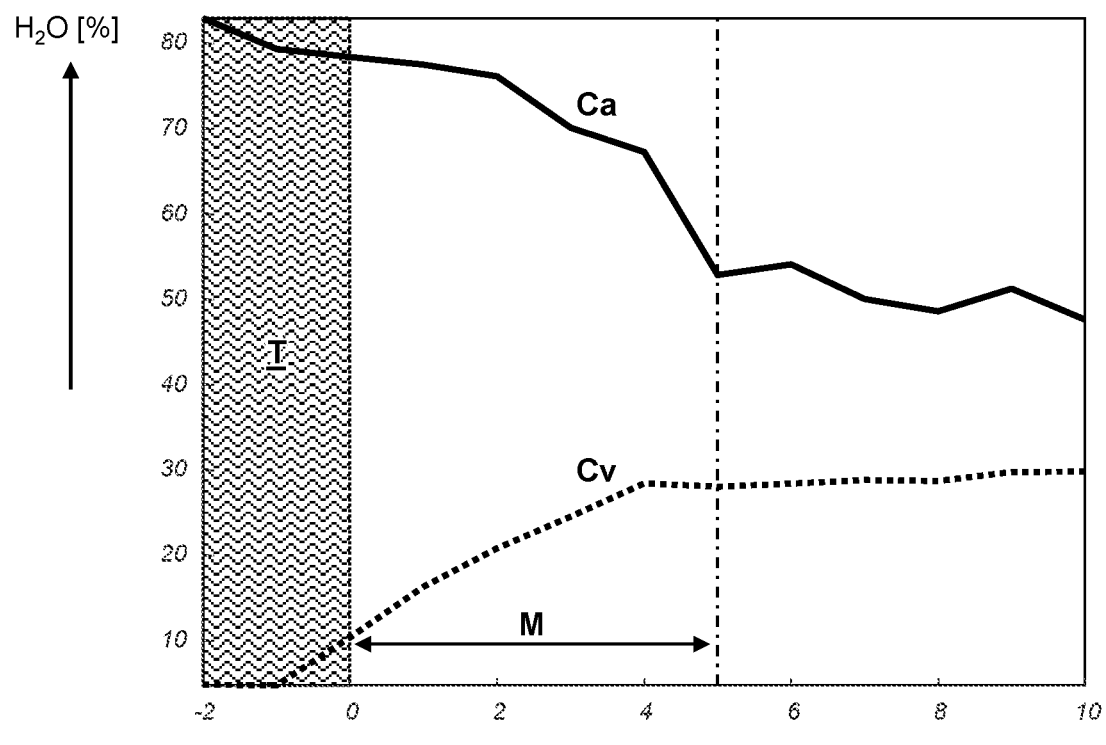
FIGS. 3A and 3B illustrate graphs of water concentrations and spatial variance.
Figure 3B:
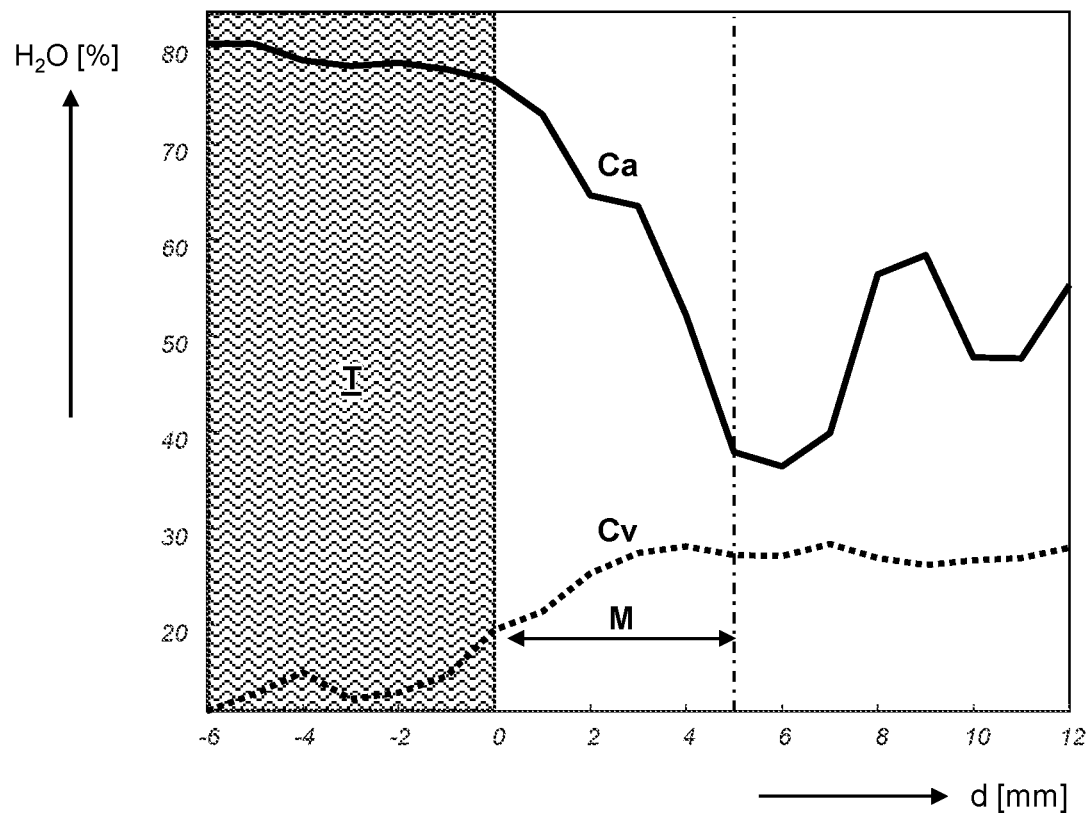

FIGS. 3A and 3B illustrate measurements of a (relative) water (H2O) concentration Ca and variance Cv for different distances "d" to the border of tumour T.

Figure 2B:
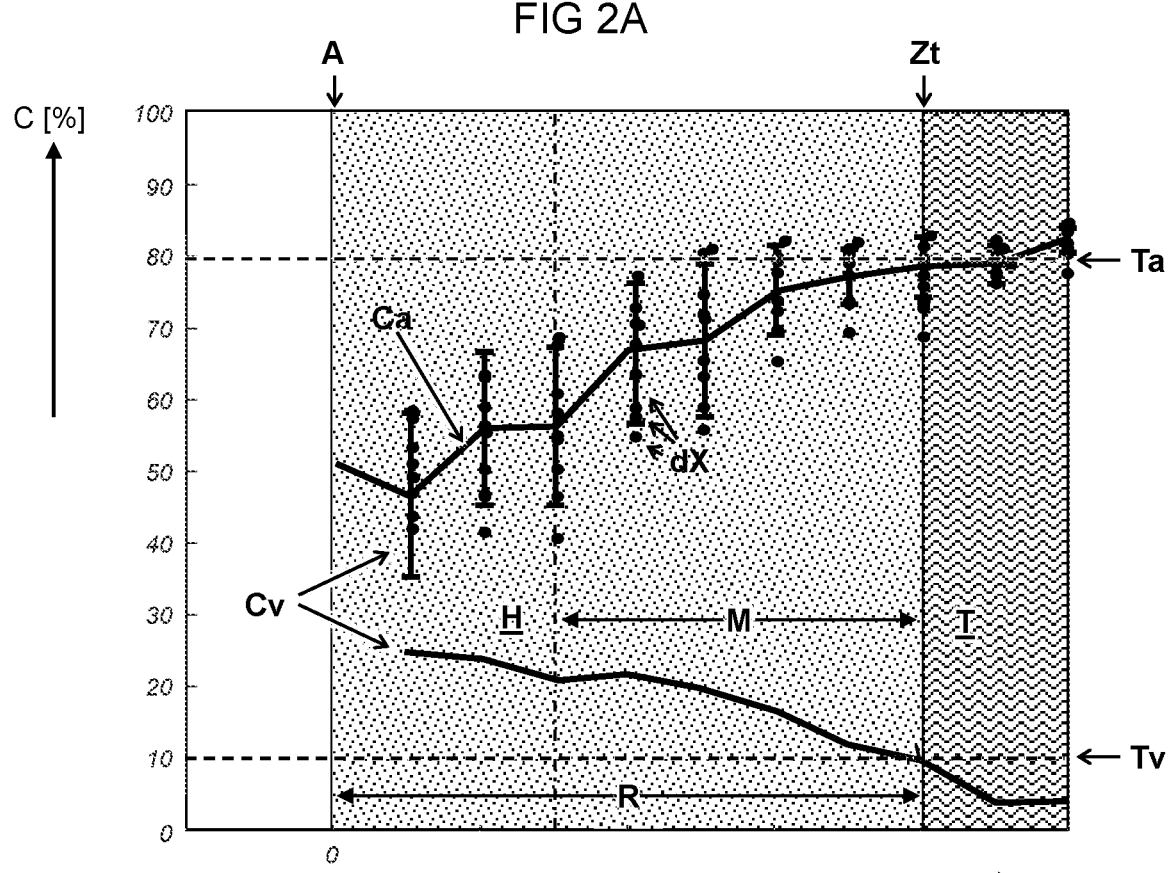

In one embodiment, a threshold variance Tv is set at a value between five and twenty-five percent, for example a tissue is classified as tumour tissue T when the standard deviation of a number of water concentration measurements, e.g. measured over a measuring distance of one millimeter in the tissue, is less than ten percent (FIG. 2A) or less than twenty percent (FIG. 2B).

In another or further embodiment, a threshold mean Ta is set at a value between seventy and ninety percent, for example a tissue is classified as tumour tissue T when the mean value of a number of water concentration measurements, e.g. measured over a measuring distance dZ of one millimeter in the tissue, is more than eighty percent.

In another or further embodiment, a threshold ratio Tm/Ta is set at a value between two and twenty, for example a tissue is classified as tumour tissue T when the ratio of the mean over the variance of a number of water concentration measurements, e.g. measured over a measuring distance dZ of one millimeter in the tissue, is more than four and half.

Figure 4:
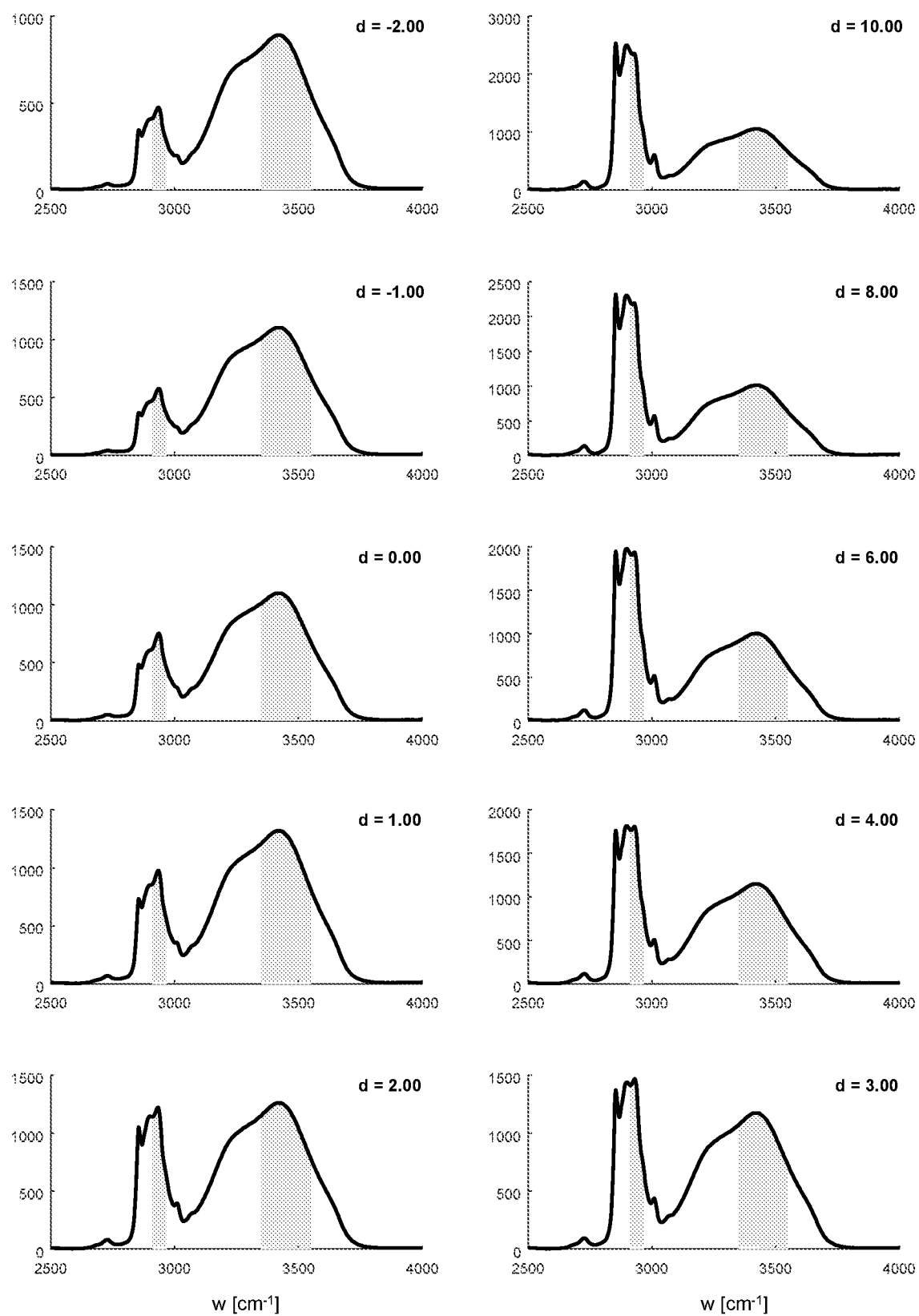
FIG. 4 illustrates Raman spectra to calculate water concentrations.

FIG. 4 illustrates Raman spectra of a tissue sample at various distances "d" from the tumour border. These spectra were used to calculate the graph of FIG. 3A.

One embodiment comprises calculating an analyte concentration based on a spectral measurement. In another or further embodiment, an analyte concentration and/or variance is calculated as a function of the depth position Z. For example, a relative concentration of a first analyte is calculated with respect to a second analyte based on relative contributions of their spectral signatures in the spectral measurements. For example, the analyte is water. In one embodiment, the calculation of water concentration may comprise using the ratio of the Raman bands at 3390 $cm^{-1}$ and 2935 $cm^{-1}$, corresponding to spectral bands of the OH and $CH_3$ stretch vibrations, respectively. Optionally, a background signal may be subtracted from the spectrum before calculating the ratio. For example a procedure for calculating water concentration based on Raman spectra is explained in an article by Caspers et al. (J. Invest. Dermatol. 2001, 3, 434-442) and an article by Wolthuis et al. (J. Anal. Chem. 2001, 73, 3915-3920).

FIGS. 5-7 illustrate various embodiments of a needle 11 comprising an optical waveguide 12.

In one embodiment, probe light is transmitted via the optical waveguide 12 through the needle at a controlled variable depth Z of the needle into the tissue surface and an optical response of the tissue sample to the probe light is measured for calculating the concentration of the analyte at the controlled variable depth Z.

In one embodiment, the needle 11 comprises one or more optical fibers forming the optical waveguide 12. For example, a needle such as described in WO 2014162289 A1 can be used. In one embodiment, an optical fiber is fixated inside a hypodermic needle, e.g. using epoxy resin 13 to fill or partly fill the space between the optical fiber and the inner wall of the hypodermic needle. The optical fiber may be inserted until the distal end of the optical fiber is at a defined distance to the tip of the needle. The distance may be chosen such that when the needle is inserted in the tissue there is direct contact between the optical fiber and the tissue. In one embodiment, the distal end of the fiber is polished. The fiber may be flat (end face perpendicular to optical axis of the fiber) or polished at an angle, e.g. flush with the angle of the needle tip. In one embodiment, the proximal fiber end is fixated in a connector, e.g. an SMA-coupler or an FC/PC coupler, and polished flush with respect to connector face, enable butt-coupling to a second optical fiber inserted into a same fiber coupler (commonly used fiber coupling techniques. In one embodiment, a bevel angle of 30°-35° provides a needle which is easy to insert and which provides a low tendency to cause tissue sticking.

For example, the optical fiber extends beyond a length of the needle 11 on a distal side of the needle 11 opposite the needle tip 11t to connect to an optical interrogator device. In one embodiment, the optical fiber is formed to transmit an excitation light signal Li into the tissue sample S and a response Raman spectrum Lr out of the tissue sample S. In another or further embodiment, the optical fiber comprises a core, a cladding and optionally a coating for transmitting light at least in a wavelength range between 600 to 1000 nanometres. Accordingly, the optical fiber is preferably formed to transmit Raman signals through the optical fiber. For example, EP 1 567 852 B1 describes various aspects of using high wavenumber Raman spectroscopy for measuring tissue. In particular, the optical fiber and signal analysis as described in EP 1 567 852 B1 may have advantageous use in the present systems and method.

Figure 5A:
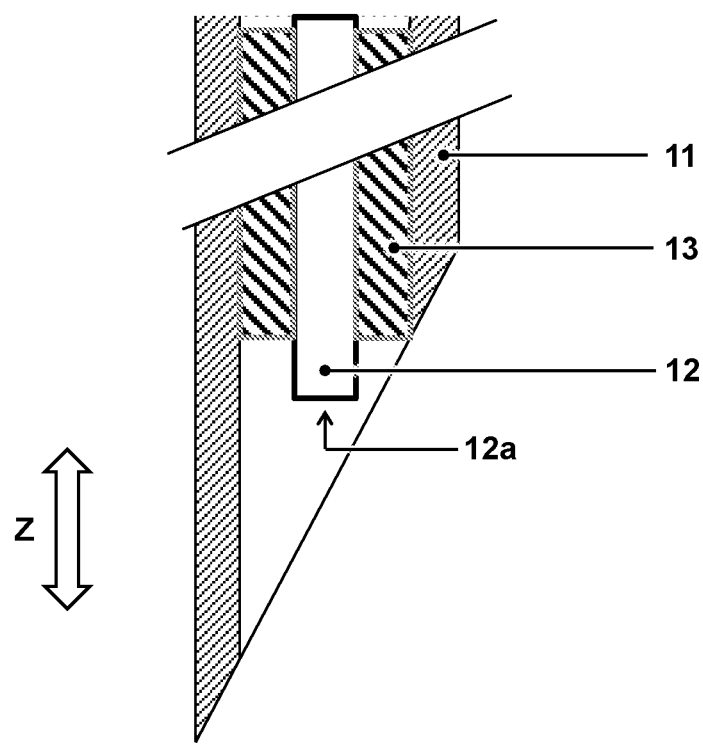
FIGS. 5-7 schematically illustrate embodiments of needles with an optical waveguide.
Figure 5B:
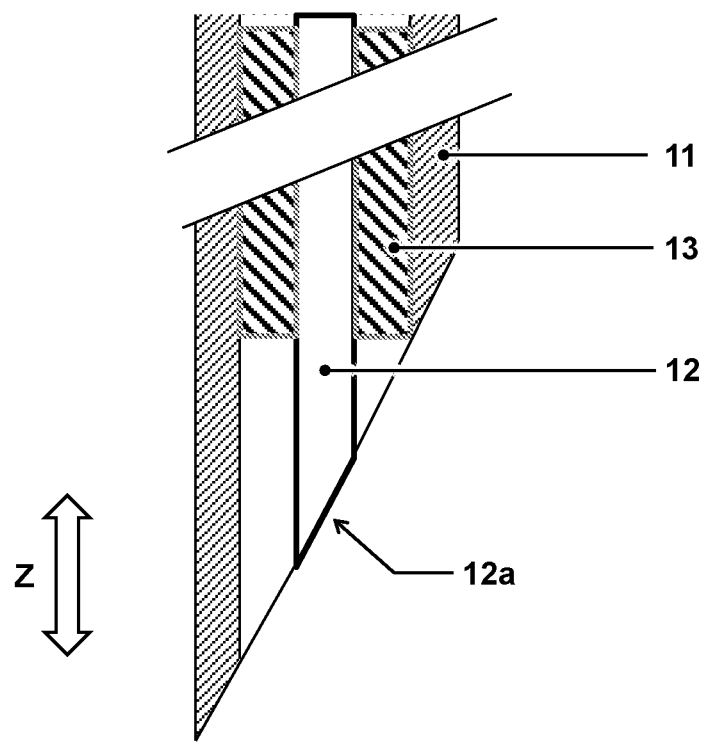

FIG. 5A illustrates an embodiment, wherein an optical fibre 12 ends with an optical interface 12a that is transverse to the depth direction Z. FIG. 5B illustrates another embodiment, wherein the optical fibre is cut at an angle flush with an angle of the needle.

Figure 6A:
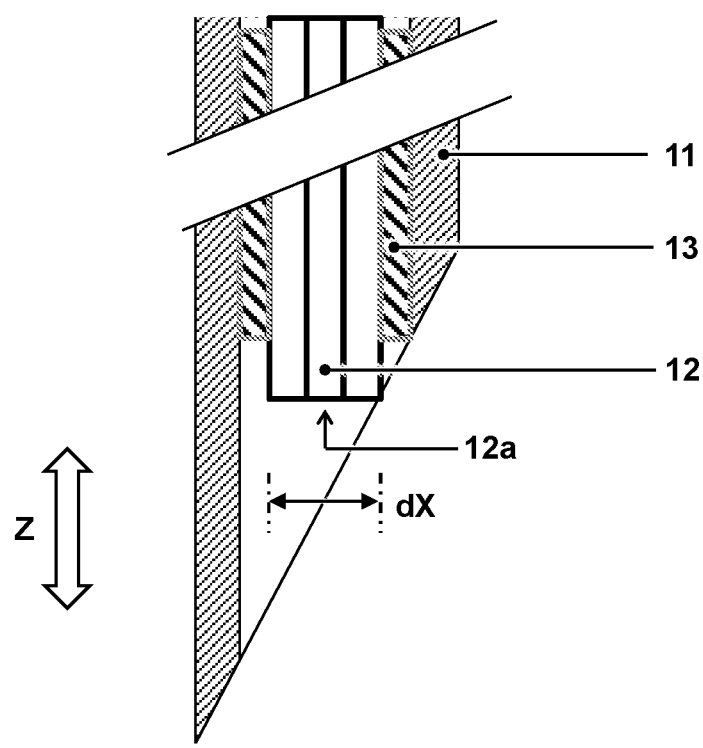
Figure 6B:
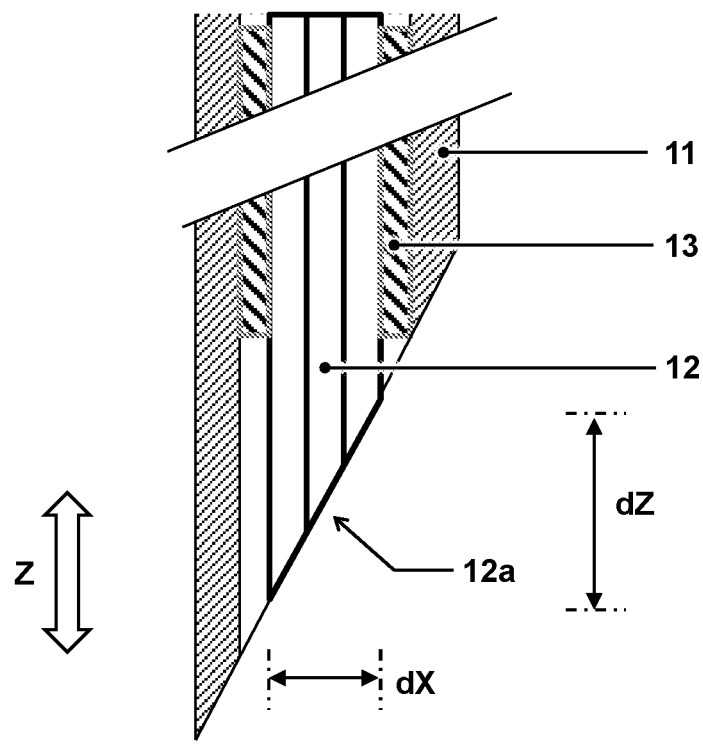

FIGS. 6A and 6B illustrate embodiments wherein the optical waveguide 12 comprises a bundle of fibres inside the needle 11. In one embodiment, adjacent optical fibres are configured to provide individual measurements of the concentration of analyte C at space apart locations dX and/or dZ in the tissue sample S.

Figure 7A:
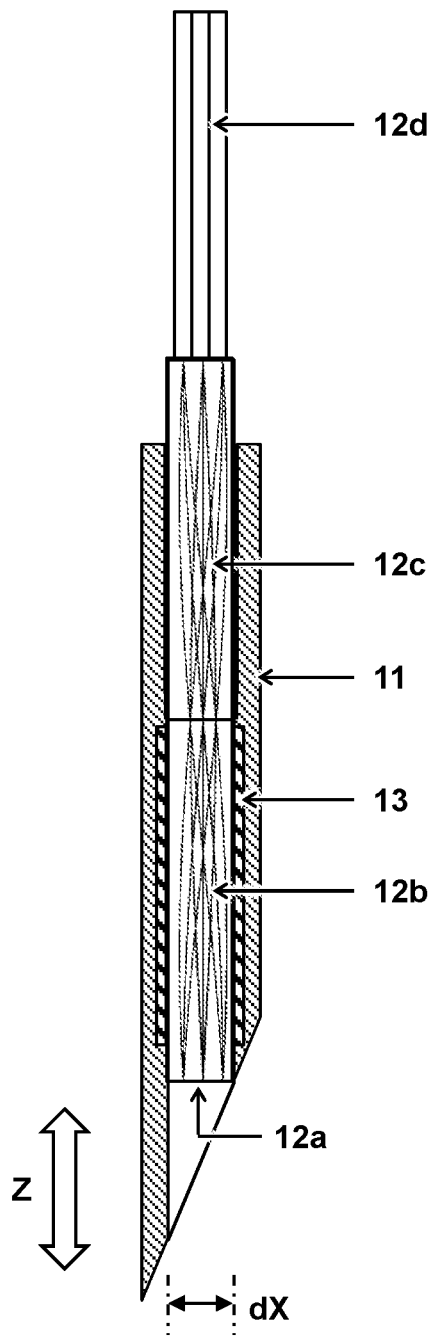
Figure 7B:
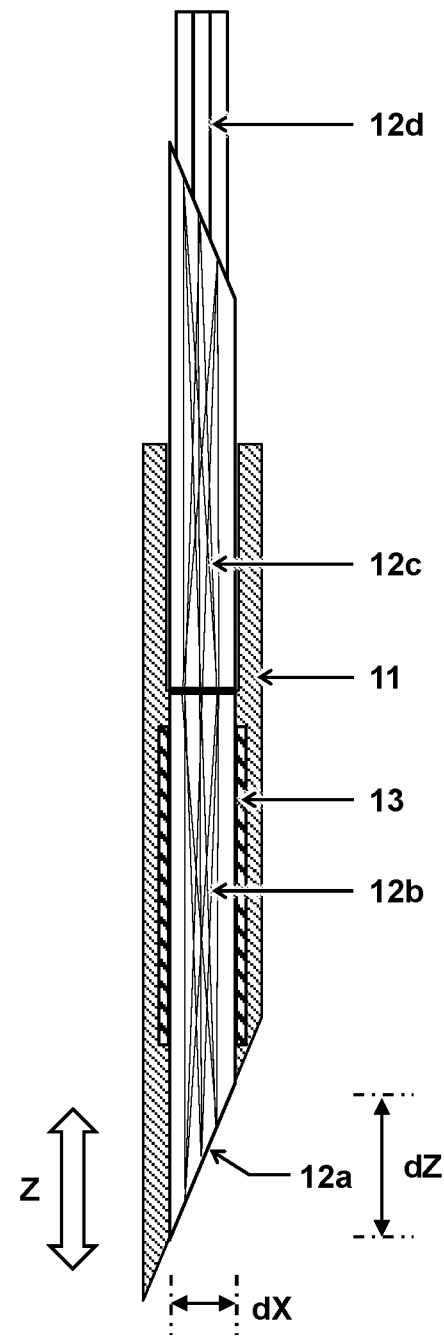

FIGS. 7A and 7B illustrates an embodiment wherein the optical waveguide 12 comprises a lens 12b,12c inside the needle 11. For example, the lens is configured to image light from a fibre bundle 12d at spaced apart locations in the tissue sample S. In one embodiment, the lens 12b,12c comprises a gradient index lens. In another or further embodiment, a first gradient index lens 12b is fixated inside the needle 11 and a second gradient index lens 12c is connected to a fibre bundle 12d. For example, the second gradient index lens 12c is connectable to a disposable needle 11 which comprises the first gradient index lens 12b. In one embodiment, the gradient index lenses 12b,12c are half-period gradient index lenses.

In the embodiment of FIG. 7A, the gradient index lens 12b is cut transverse to the depth direction Z. In the embodiment of FIG. 7B, the gradient index lenses 12b,12c are cut at an angle. For example, the first gradient index lens 12b comprises an light exit surface 12a that is at an angle flush with an angle of the needle 11.

Figure 8:
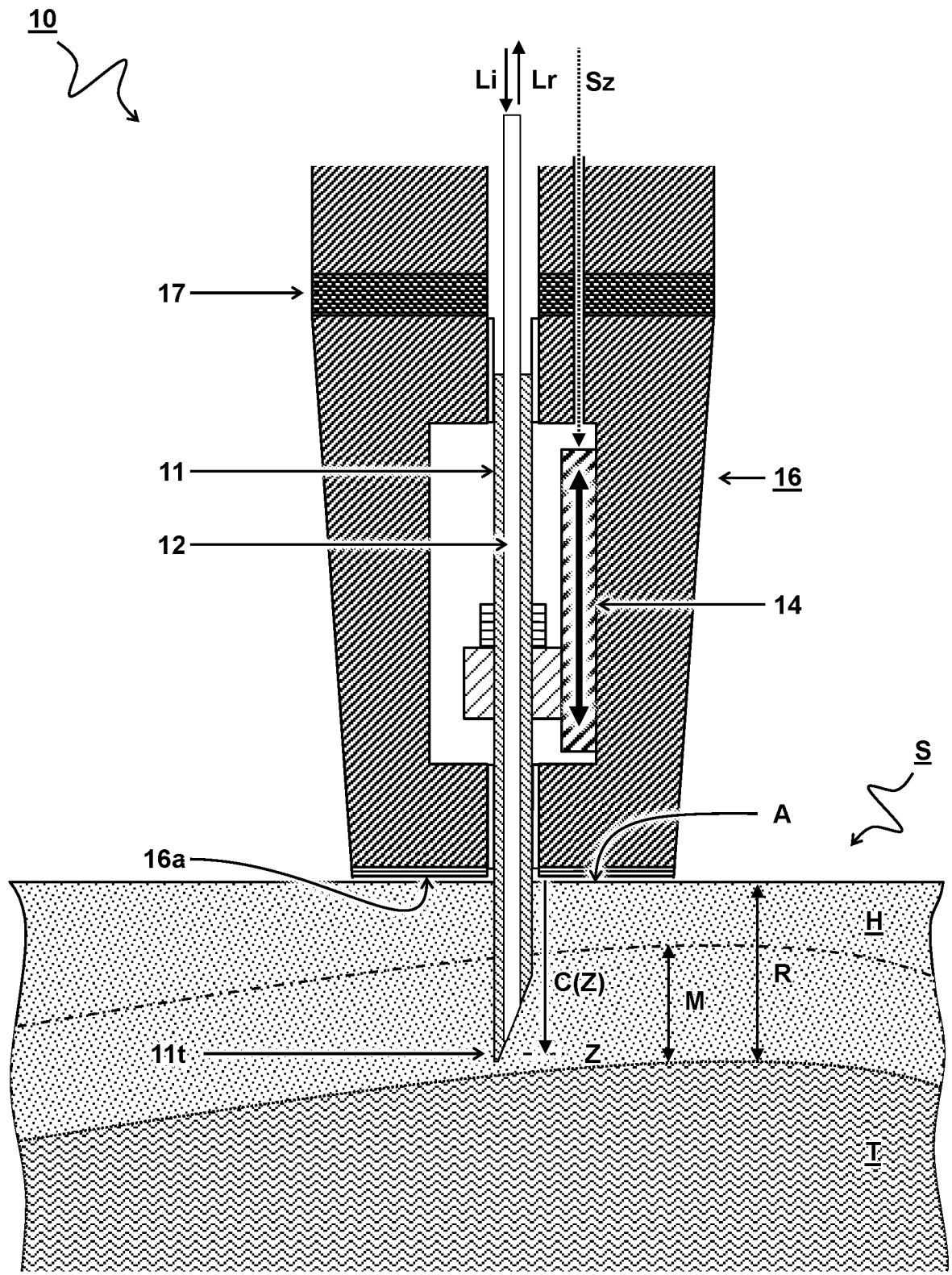
FIG. 8 schematically illustrates a cross-section view of a first embodiment of an optical probe for measuring a tissue sample.

FIG. 8 schematically illustrates a cross-section view of an embodiment of an optical probe 10 for measuring a tissue sample S.

In one embodiment, the optical probe 10 comprises a needle 11 having a needle tip 11t formed to penetrate a tissue surface "A". The needle further comprises an optical waveguide 12 arranged to transmit light Li,Lr through the needle 11. For example, the needle and waveguide may be constructed according to any of the embodiments described with reference to FIGS. 5-7

In one embodiment, the optical probe 10 comprises a probe housing 16 for holding the needle 11. For example, the probe housing 16 comprises an actuator 14 configured to receive a depth signal Sz to determine a depth position Z of the needle tip 11t relative to the tissue surface "A". In some embodiments, the actuator may also act as sensor or a sensor can be added to measure the depth position Z of the needle.

In one embodiment, methods of measuring the tissue sample S are performed ex-vivo on a resected tissue specimen. For example the tissue sample S is measured intraoperatively. For example, when the tissue T is excised as a procedure to remove a tumour, the region H may correspond to a healthy tissue while the region T may correspond to a tumour tissue. There may be an intermediate region in a margin M where there is a chance that tumour tissue has partly grown into the healthy tissue. For improved chances of success, it is desired to cut out the tumour tissue with a certain margin of healthy tissue around the tumour to prevent recurrence of the tumour.

In one embodiment, the probe housing 16 comprises a tissue engaging surface 16a. In another or further embodiment, the probe housing 16 comprises a needle guiding structure configured to guide the needle 11 transverse to the tissue engaging surface 16a. For example, the depth signal Sz is calculated as a function of a variable distance between the needle tip 11t and the tissue engaging surface 16a. Preferable, the needle guiding structure is configured to sliclingly engage the needle. Also other guiding structures can be used, e.g. rollers. In one embodiment, the needle 11 is configured to slide through the needle guiding structure between a retracted position fully inside the probe housing 16 and an extended position out of the probe housing and into the tissue sample S.

In one embodiment, the actuator 14 is configured to actuate the needle 11. Accordingly, the depth signal Sz is an input signal of the actuator 14 to provide an absolute or relative position of the needle tip 11t with respect to the tissue surface "A" and/or the tissue engaging surface 16a. In another or further embodiment, the actuator 14 comprises a translation stage with a moveable stage mount 14a wherein the stage mount 14a is attached to the needle 11 and/or needle mount 11a. In a further embodiment, the probed comprises a depth signal wire 14w configured to transmit the depth signal Sz to the actuator 14 to control actuation of the depth position Z of the needle. For example an electrical wire can be used.

In one embodiment, the optical probe 10 comprises a pressure sensor 17 configured to determine a contact between the tissue engaging surface 16a and the tissue surface "A". In another or further embodiment, a pressure signal wire 17w is configured to transmit a pressure signal Sp indicative of the contact between the tissue engaging surface 16a and the tissue surface "A". In another or further embodiment, the actuator 14 is configured to actuate the needle 11 upon detection of contact between the tissue engaging surface 16a and the tissue surface "A".

In another embodiment (not shown), the probe housing 16 comprises a sensor configured to generate a depth signal Sz to determine a depth position Z of the needle tip 11t relative to the tissue surface "A". Accordingly, the sensor may be configured to measure the depth position Z of the needle tip 11t. In one embodiment, the depth signal Sz is calculated from an output of the sensor which is configured to measure a translation of the needle 11 relative to the tissue engaging surface 16a and/or the tissue surface "A". In one embodiment, the tissue engaging surface 16a is moveable with respect to the needle 11. In another or further embodiment, the sensor is configured to measure a translation of the tissue engaging surface 16a.

In another embodiment (not shown), a sensor is configured to measure a distance between a front of the probe housing 16 and the tissue surface "A". For example, the depth signal Sz is calculated by subtracting the measured distance from a known distance between the needle tip 11t and the front of the probe housing 16. Also other distance sensors may be used. Alternative or in addition to the distance sensor, a pressure sensor 17 can be configured to detect when the needle 11 comes into contact with the tissue surface. Alternatively, or in addition, a contact sensor can be used, e.g. a capacitive sensor connected to the needle to determine contact with the tissue. Also the amount of contact (depth of the needle) may be determined e.g. by measuring capacitance and or conductance. The depth position Z can be determined e.g. by measuring and/or controlling the actuated distance from the point of contact with the tissue surface "A". The optical probe 10 can e.g. be used in an automated instrument wherein the whole probe is moved. The needle 11 can be stationary with respect to the probe housing 16, e.g. attached via a needle mount 11a.

Also other combinations and variations of the optical probe 10 are possible. For example, in one embodiment (not shown) the optical probe 10 comprises an array of needles configured to simultaneously perform measurements at different locations over the tissue surface "A". The instrument may also comprise additional actuators, e.g. rollers to rotate the tissue specimen for measuring different sides of the tissue specimen.

Figure 9:
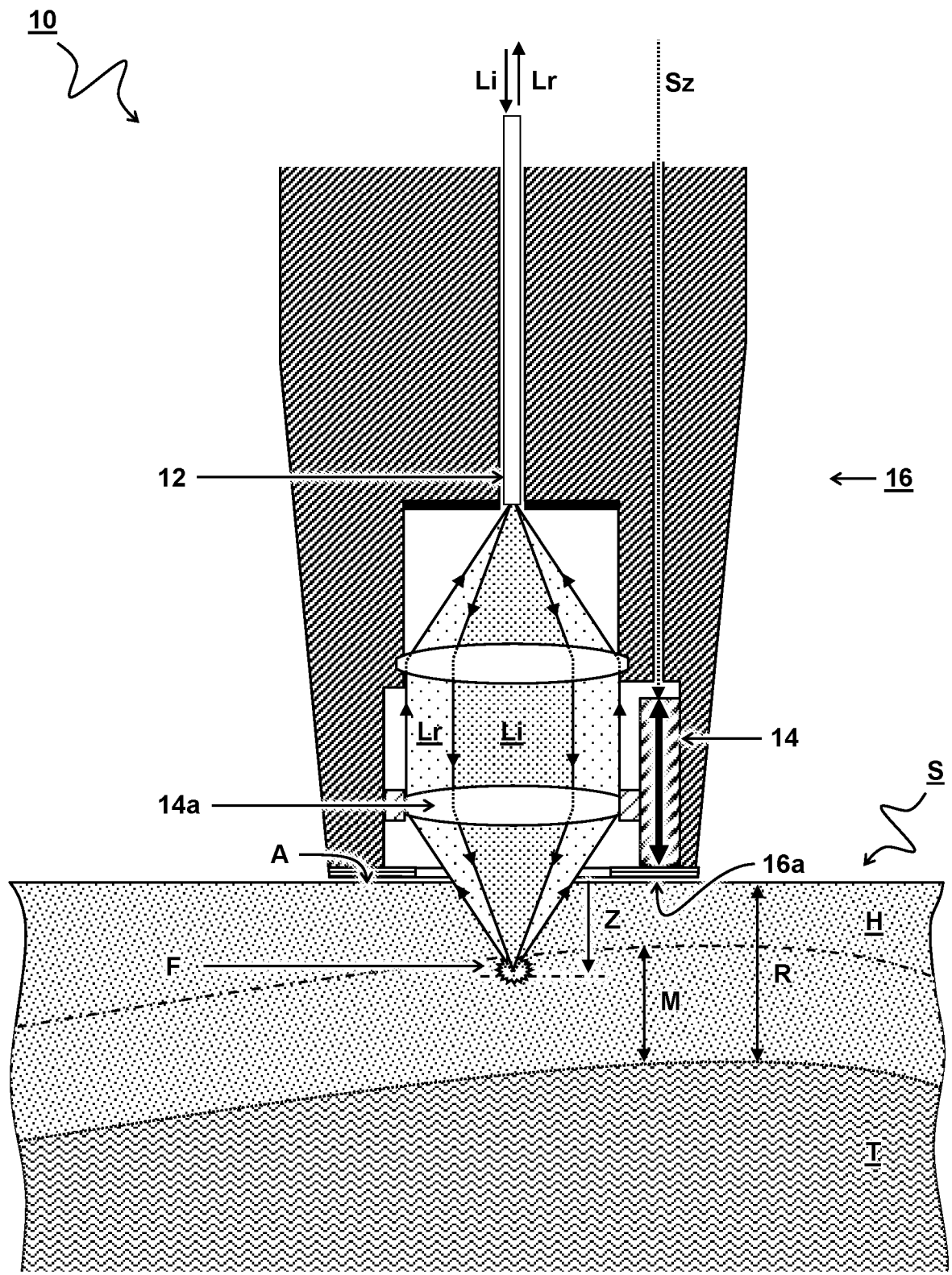
FIG. 9 schematically illustrates a cross-section view of a second embodiment of an optical probe for measuring a tissue sample.

FIG. 9 illustrates another embodiment of an optical probe 10 for measuring a tissue sample.

In one embodiment, the measuring of the localized concentration is performed using a confocal optical system. For example, probe light Li is transmitted at a controlled variable depth Z into the tissue surface A by varying a distance of a focal point F of probe light below the tissue surface A and an optical response Lr of the tissue sample S to the probe light Li is measured for calculating the concentration of the analyte at the controlled variable depth Z. For example, the distance of the focal point F is varied by a moveable lens 14a which may be connected to an actuator 14.

Figure 10:
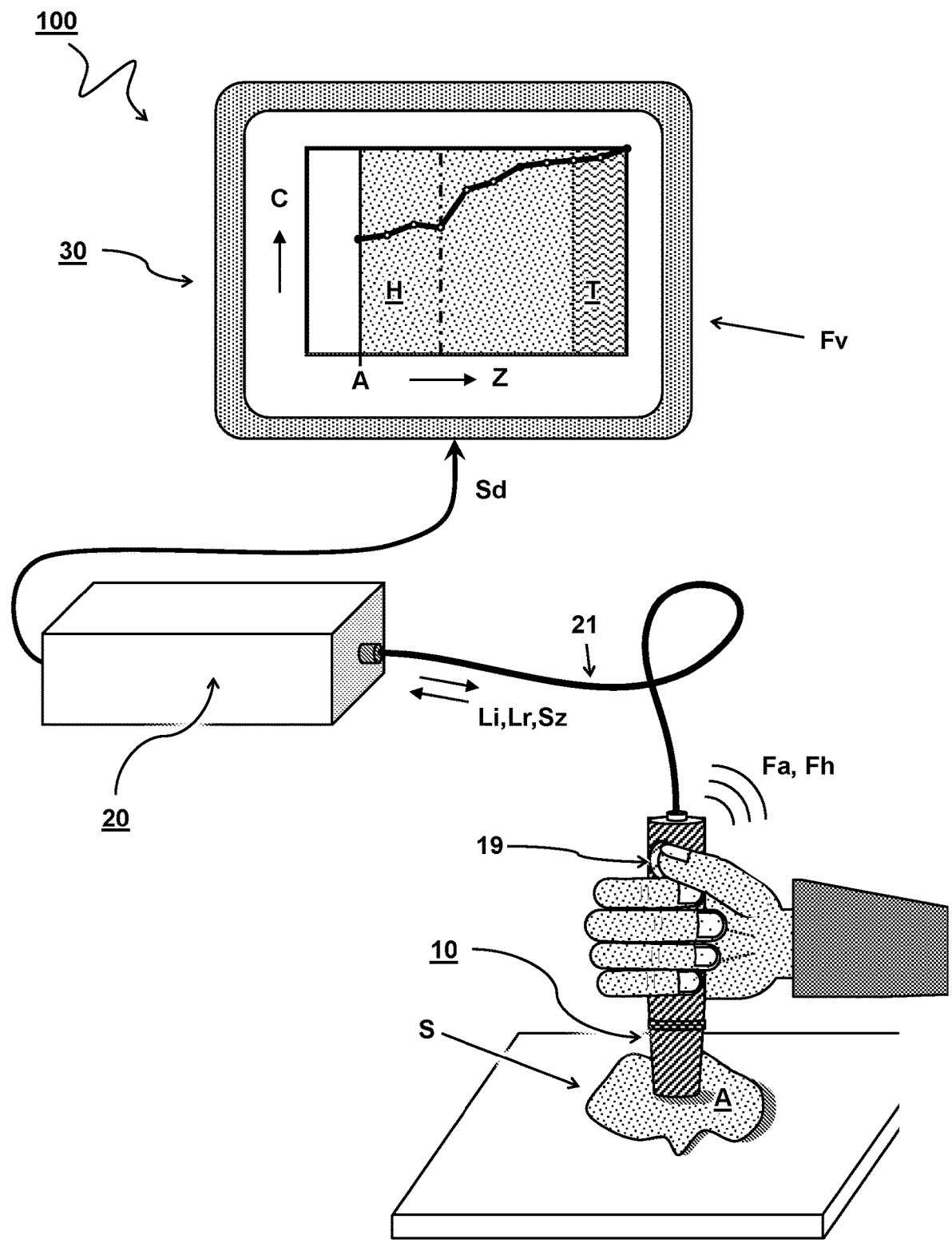
FIG. 10 schematically illustrates a perspective view of a first embodiment of an instrument for measuring a tissue sample.

FIG. 10 schematically illustrates a perspective view of an embodiment of an instrument 100 for measuring a tissue sample S.

In one embodiment, the instrument 100 comprises a probe 10 configured to set a variable controlled measuring depth Z below a surface A of the tissue sample S to measure a localized concentration of an analyte C at a plurality of spaced apart locations around the controlled depth Z. In another or further embodiment, the instrument comprises or couples to a controller configured to calculate a spatial variance Cv of the concentration of the analyte as a function of the controlled depth Z. For example, the controller comprises or couples to a computer readable medium with software instructions that when executed by the instrument 20 causes execution of a method as described herein.

In one embodiment, the instrument 100 comprises the optical probe 10, e.g. as described herein, and an interrogator 20 configured to provide an input light signal Li to the optical probe 10 and measure a response light signal Lr from the optical probe 10 as a function of a depth position Z of the needle in the tissue sample S. In one embodiment, the optical probe 10 is connected to the interrogator 20 via an optical cable configured to transmit the light signals Li,Lr for measuring a spectrum of the tissue sample S. In another or further embodiment, the optical probe 10 is connected to the interrogator 20 via an electrical cable configured to transmit the depth signal Sz for determining a depth position Z of the needle corresponding to the measured spectrum. The depth signal may also be transmitted as an optical signal.

In one embodiment, the optical probe 10 comprises a hand grip portion to hold the optical probe 10 by hand (H) and engage the optical probe 10 with the tissue sample S to perform the measurement. Accordingly, the optical probe 10 can be a hand-held device. In another or further embodiment, the optical probe 10 comprises a button 19 to initiate a measurement. For example, the button 19 activates an actuator and/or releases a safety mechanism to allow the needle to extend from the probe housing.

In one embodiment, the instrument 100 comprises or couples to a display screen 30 to display the measurement. In the shown embodiment, the interrogator 20 directly connects to a display screen. Alternatively, or in addition, the interrogator 20 may connect to a computer running software that controls the interrogator 20 and/or receives data output from the interrogator 20. The display screen may be connected to the computer. The computer may also be considered part of the interrogator.

In one embodiment, a feedback signal Fa is provided based on a comparison between the calculated section distance R and a pre-set minimum section margin M. For example, the feedback comprises one or more of a visual feedback Fv, audio, feedback Fa, or haptic feedback, Fh when the tissue sample S is classified as inadequately resected.

Figure 11:
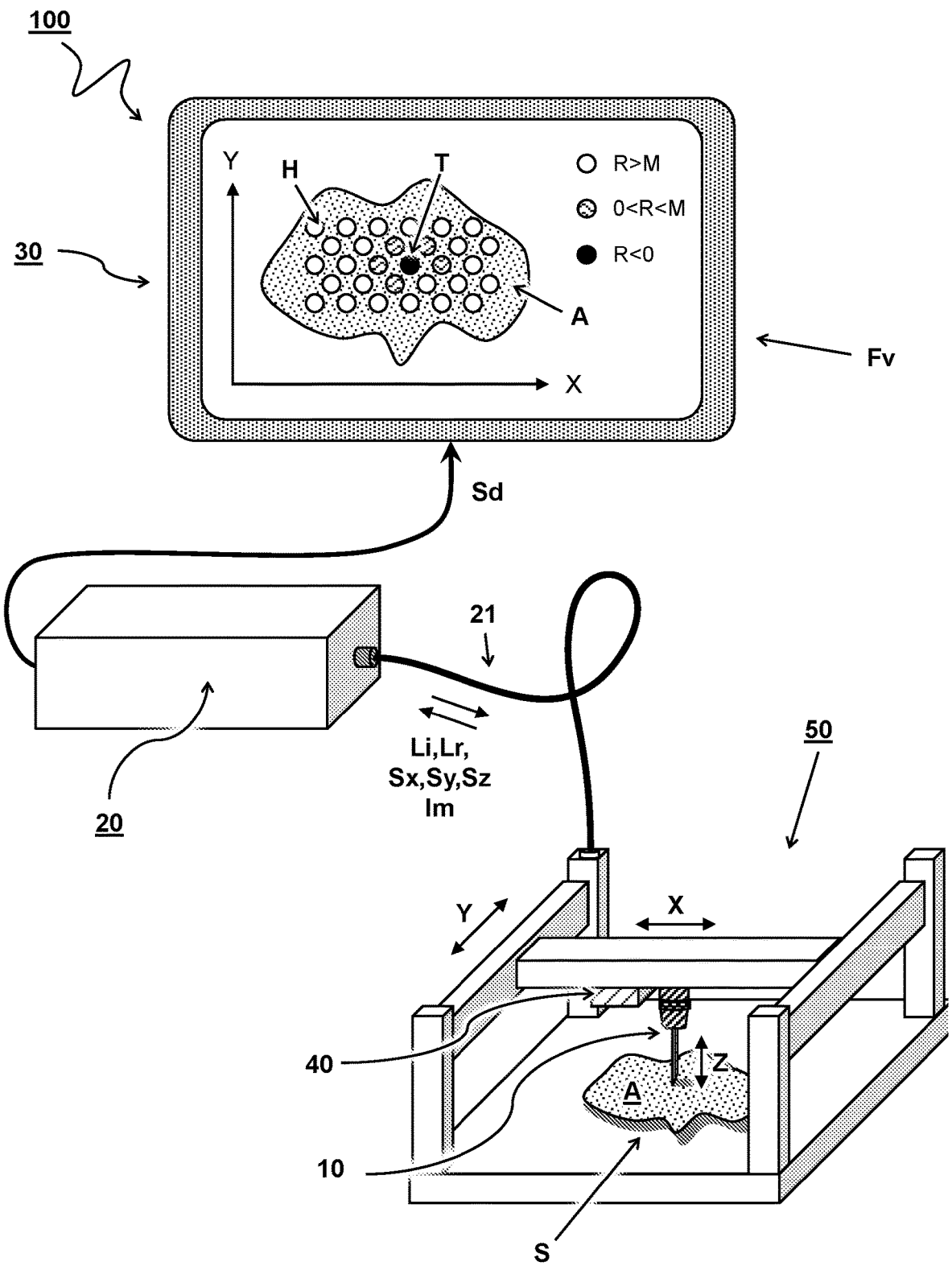
FIG. 11 schematically illustrates a perspective view of a second embodiment of an instrument for measuring a tissue sample.

FIG. 11 schematically illustrates a perspective view of a second embodiment of an instrument 100 for measuring a tissue sample S.

In one embodiment, the instrument 100 comprises an actuator table 50 comprising one or more actuators. For example, the instrument 100 comprises a z-actuator configured control the depth of the needle with respect tot the tissue surface to perform automatic measurement at different depths. For example, the instrument 100 comprises an xy-actuator configured to scan a tissue surface and perform spectral measurements at different locations. The actuators may be controlled by the interrogator 20 and/or further hardware e.g. using corresponding control signals Sx,Sy,Sz.

In one embodiment, the instrument 100 comprises a digital camera 40 configured to record and/or transmit a picture "Im" of the tissue sample S under investigation. In another or further embodiment, the interrogator 20 (or computer) is configured to generate an image wherein the picture of the tissue surface "A" is overlaid with one or more indicators of tissue measurements performed by the optical probe 10. For example, a picture of the tissue surface A is overlaid with visual indicators (e.g. color dots) of the spectral signatures as a function of position (X,Y) on the tissue. Accordingly, positions of the indicators in the image may correlate with positions of a measurements on the tissue sample S. For example, different indicators may be displayed as a function of a depth dependent spectral measurement. For example, the visual indicators are generated as a function of a margin of healthy tissue surrounding the tumour tissue. In one embodiment, the instrument may provide an option to select regions of interest in the picture for additional measurements. Accordingly, a quick measurement can be taken over the tissue surface followed by a specific measurements at regions of interest.

Figure 12:
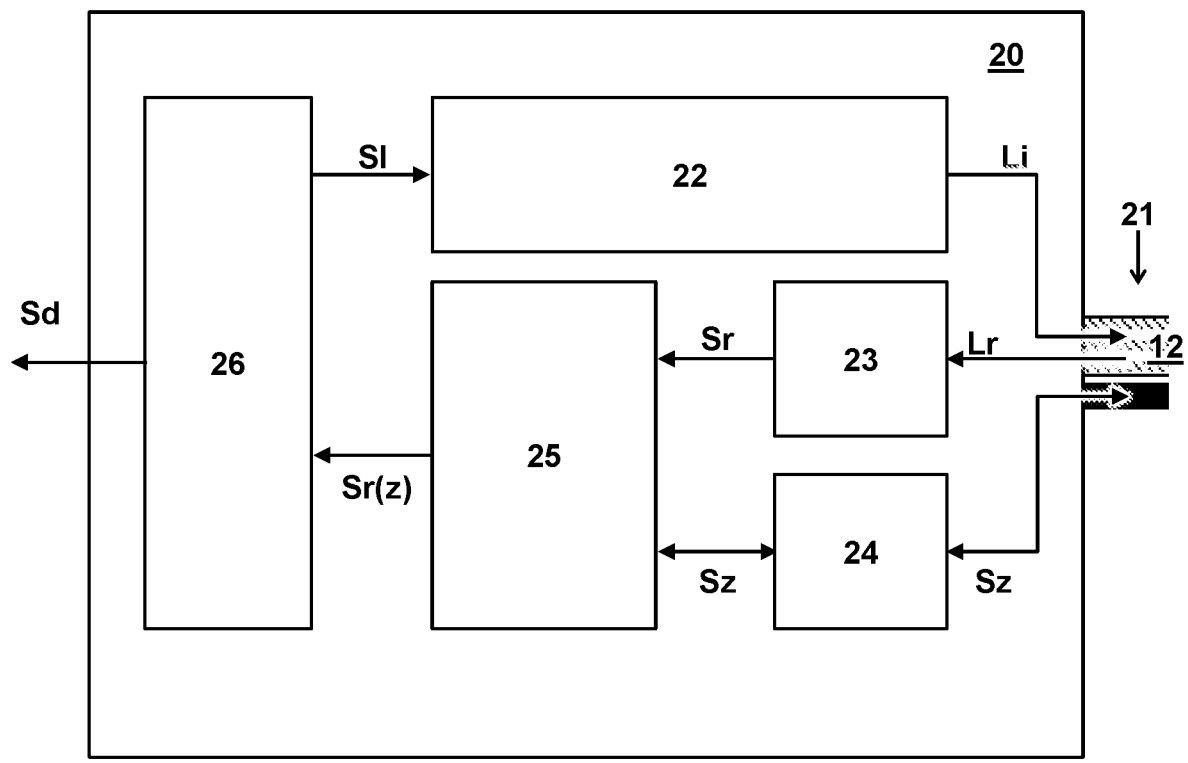
FIG. 12 schematically illustrates a diagram of an embodiment of an interrogator for measuring a tissue sample.

FIG. 12 schematically illustrates a diagram of an embodiment of an interrogator 20 for measuring a tissue sample.

In one embodiment, the interrogator 20 comprises a light source 22 configured to provide the input light signal Li into the optical waveguide 12 for probing inside the tissue sample. For example, the light source 22 may comprise a laser configured to generate a Raman inducing light input signal Li.

In one embodiment, the interrogator 20 comprises a light sensor 23 configured to receive a response light signal Lr from the optical waveguide 12 indicative of a response of the tissue sample S to the input light signal Li. For example, the light sensor 23 may comprise a pixel array to record a light spectrum. In another or further embodiment, the interrogator 20 comprises a dispersion or diffraction element (not shown) to spectrally resolve the response light signal Lr on the light sensor 23.

In one embodiment, the interrogator 20 comprises a depth control circuit 24 configured to determine the depth signal Sz and calculate the depth position Z of the needle tip 11t with respect to the tissue surface "A". For example, the circuit 24 may comprise an actuator control to control an actuator attached to the needle. For example, the circuit 24 may comprise a depth sensor readout to receive and/or process sensor signals indicating the depth of the needle.

In one embodiment, the interrogator 20 comprises an analyser 25 configured to determine a plurality of measurements of the tissue sample S as a function of the depth position Z in the tissue sample S, e.g. based on the response light signal Lr as a function of the depth signal Sz. Functionality of the analyser may be provided by software and/or hardware components.

In one embodiment, the interrogator 20 comprises a controller 26 configured to coordinate a depth of the needle, wherein the controller stores the measurements as a function of depth. For example, the interrogator 20 comprises or couples to a storage device, e.g. memory, to store data. The controller may be a dedicated or all-purpose processor. The controller may be loaded with software instructions to cause it to perform operational acts in accordance with the present methods and systems.

For some types of cancer, a tumour tissue may be distinguished from a healthy tissue by an analyte concentration and/or variance. For example, a tumour tissue T may have a higher water concentration and lower water variation than healthy tissue H. In one embodiment, a margin "M" (safety distance) around the tumour tissue T is calculated based on the depth dependent analyte concentration. For example a safety margin or at least 5 millimetres may be preferably to increase chances that the tumour is completely resected. The tissue having a section distance R where 0<R<M may be intermediate tissue which may or may not have tumour growth.

Figure 13:
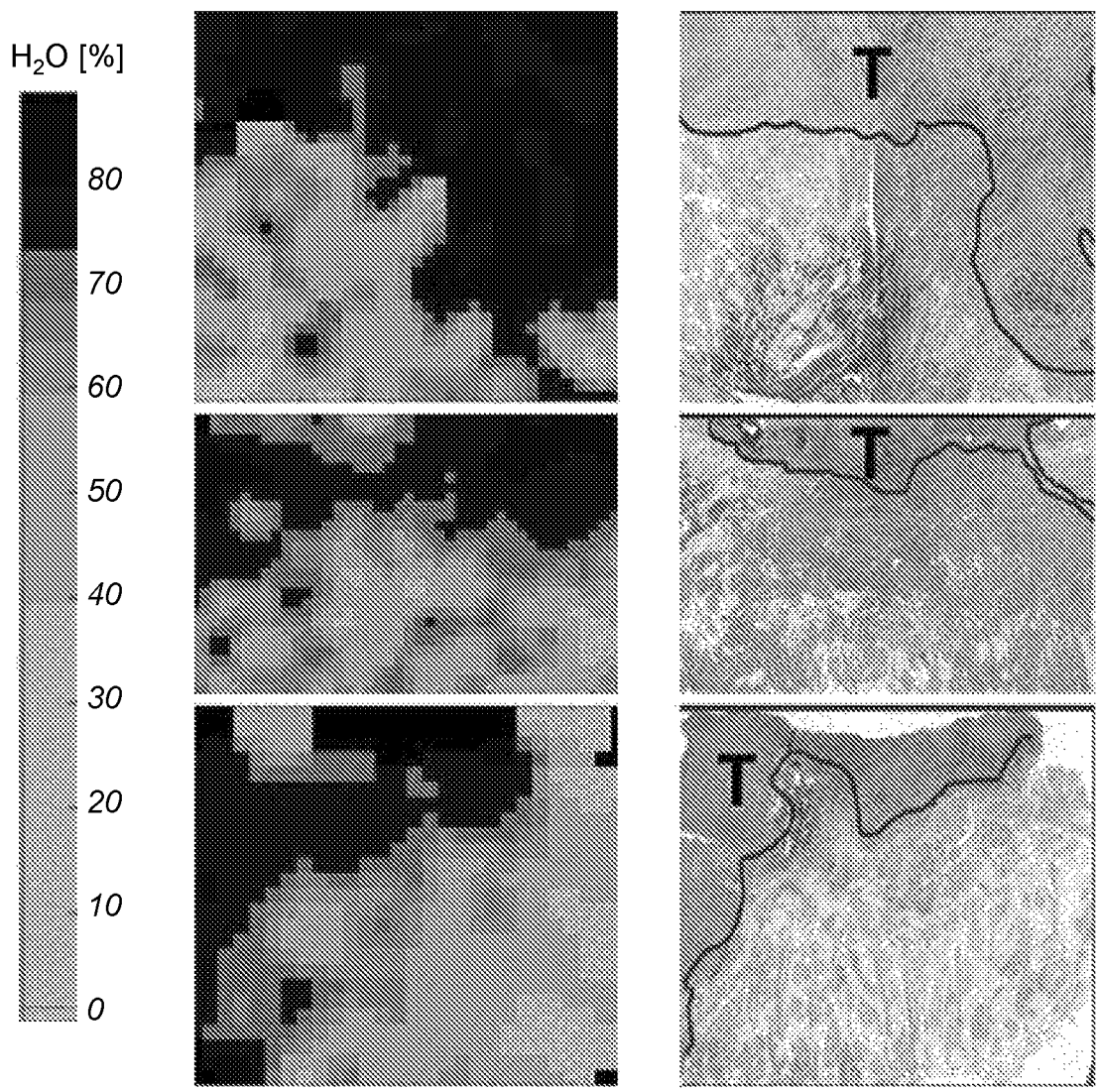
FIG. 13 illustrates a correlation between tumour tissue and water concentration.

FIG. 13 illustrates examples of the correlation between the water concentration profile (left) and the definitive histopathological classification of resection tissue (right) taken during surgery for removal of OCSCC.

It will be noted that the location of the change in water concentration between OCSCC and its surrounding healthy tissue clearly coincides with the tumour border as follows from a comparison of the water concentration maps obtained by Raman spectroscopy on fresh resection tissue and the images of the tissue section obtained after fixation of the tissue and H&E staining. (T denotes tumour)

Figure 14A:
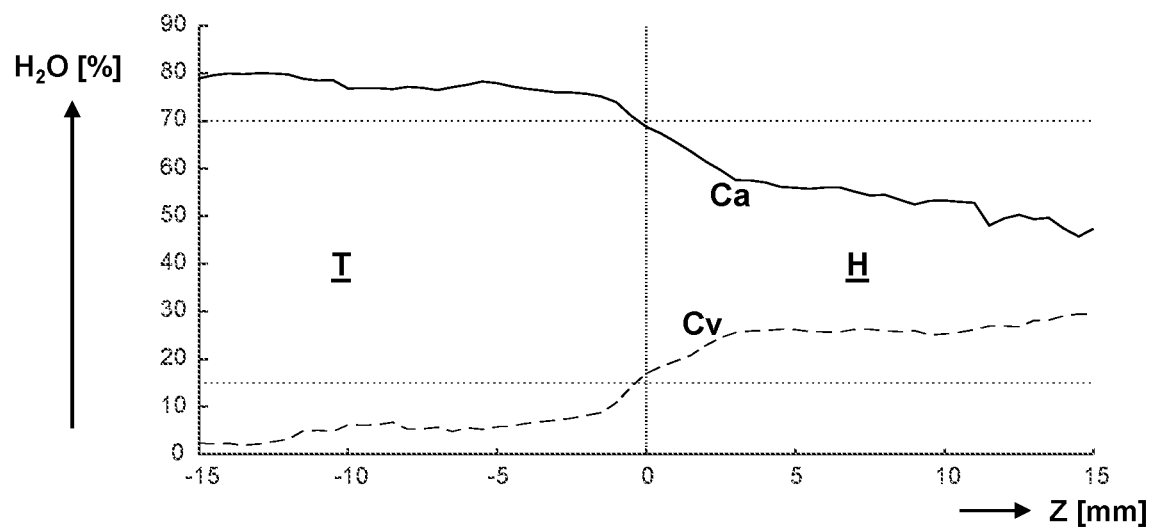
FIGS. 14A-C illustrate graphs showing the correspondence between OCSCC tumour tissue and measured water concentrations.
Figure 14B:
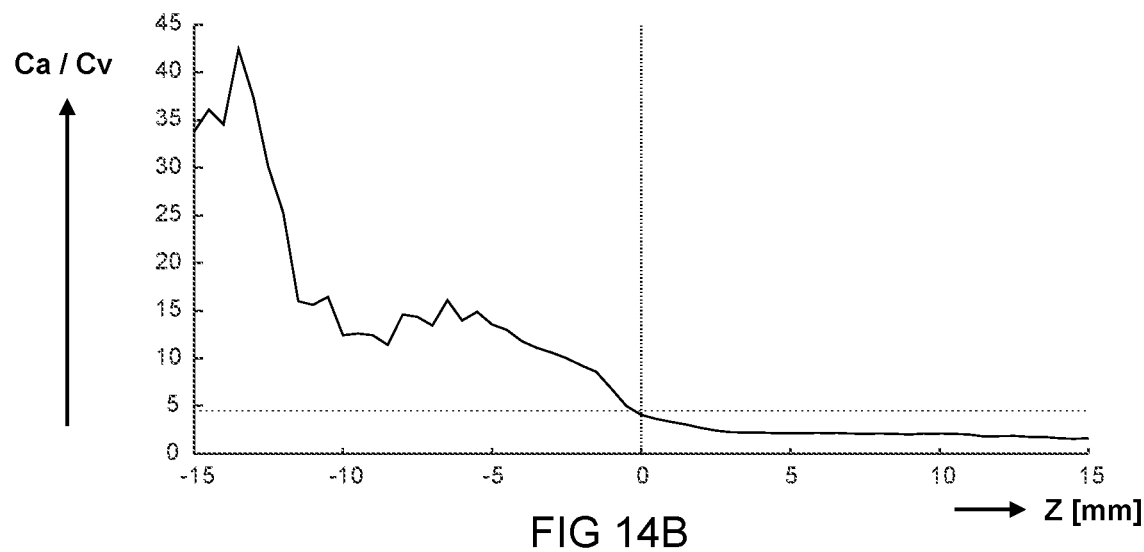
Figure 14C:
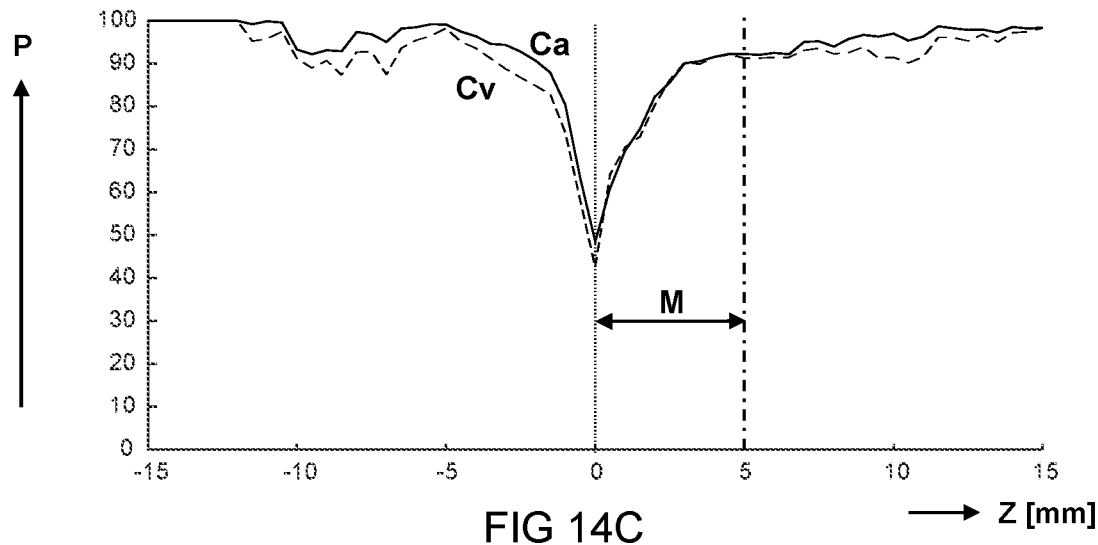

FIGS. 14A-C illustrate graphs showing the correspondence between OCSCC tumour tissue and measured water concentrations (mean value Ca and variance Cv).

FIG. 14A illustrates the mean Ca (solid line) and variance Cv (dashed line) of a 7-point water concentration measurement as a function of the distance to the tumour border. The dotted vertical line at Z=0 represents the tumour border. The dotted horizontal lines at 15% and 70% represent the best discrimination thresholds for the variance and the mean of the water concentration respectively.

FIG. 14B illustrates he ratio between mean and variance (Ca/Cv) of a 7-point water concentration measurement as a function of the distance to the tumour border. The dotted vertical line at 0 represents the tumour border. The dotted horizontal line at 4.5 represents the best discrimination threshold.

FIG. 14C illustrates Tumour vs normal tissue prediction accuracy "P" calculated from the tissue classifications as function of distance to the tumour border based on the mean (solid line) or the variance (dashed line) of a 7-point measurement of the water concentration.

In order to use variance in water concentration as a marker to discriminate between tumour and normal tissue water concentration measurements at different, closely spaced, tissue locations may be taken.

In this example, cross sections of resection specimen from fresh surgical excisions of Oral Cavity Squamous Cell Carcinoma (OCSCC) were examined. The water concentration in the cross sections was mapped by means of Raman spectroscopy, using a distance of 100 microns or more between measurement locations. After tissue fixation and staining histopathological examination was used to determine the boundary between tumour and normal tissue in these resection specimen cross sections.

In this way for each point measurement in the cross section the histopathological classification (normal or tumour) and the distance to the tumour border are known.

For each measurement point the water concentration average (Ca) and the water concentration variance (Cv) in the area surrounding and including this point were determined, based on the water concentration values of said measurement point and the 2, 4 or 6 closest measurement points (i.e. respectively 3, 5, and 7 measurements points).

As a measure for the variance we used the standard deviation defined as $$C_v = \sqrt{\frac{1}{(n-1)}\sum_{i=1}^{n}(x_i - C_a)^2}$$

where n is the number of measurements, and xi represents the water concentration at measurement location i.

The mean water concentration, m, is defined as:

$$C_a = \frac{1}{n}\sum_{i=1}^{n}x_i$$

For a range of distances to the tumour border said mean Ca and said standard deviation Cv were calculated for 3, 5, and 7 measurements at different closely spaced locations; The resulting values were averaged over 1000 measurement locations. FIG. 14A shows that OCSCC contains more water than surrounding normal tissue. At the tumour border, the average water concentration is about 70%. At the tumour border the average absolute variance in water concentration is about 15%. The ratio between said average water concentration and said average absolute variance in water concentration is 70%:15%=about 4.5. In the tumour this ratio is 80%:5%=about 16. In the normal tissue this ratio is about 60%:25%=about 2.4

The tumour vs normal prediction accuracy was determined by comparing the values of said mean Ca and said standard deviation Cv at said range of distances to the tumour border to the tumour border threshold values:

If the mean Ca is higher than, or equal to 70%, the tissue is classified as tumour; if the mean is lower than 70%, the tissue is classified as normal.

If the standard deviation Cv is lower than, or equal to 15% the tissue is classified as tumour; if the standard deviation is higher than 15%, the tissue is classified as normal.

If the ratio between average water concentration and absolute variance in water concentration (Ca/Cv) is <4.5 the tissue is classified as healthy; If the ratio between average water concentration and absolute variance in water concentration is >4.5 the tissue is classified as tumour (FIG. 2)

Some embodiments may include one or more of the following features or procedures.

1) Determination of Ca and Cv by means of multiple simultaneous water concentration measurements at substantially the same distance to the tumour border. For example, this is performed using a fiber optic needle probe, comprising a fiber bundle consisting of a number of suitably spaced optical fibers, each guiding laser light to the tissue and each fiber collecting Raman scattered light from the tissue and guiding this back to a spectrometer for analysis. Thus providing water concentration values at multiple closely spaced tissue locations. Preferably the distance between measurement points is small compared to the required precision of determining the distance between the resection surface and the tumour border.

2) Determination of Ca and Cv by means of multiple water concentration measurements at closely spaced different distances to the tumour border. For example, this is performed using a fiber optic needle probe comprising a single optical fiber for guiding laser light to the tissue and for collecting Raman scattered light from the tissue and guiding this back to a spectrometer for analysis. The fiber optic needle probe collecting tissue Raman spectra at a number of closely spaced distances, enabled by inserting the needle further into the tissue. Thus providing water concentration values at multiple closely spaced tissue locations. Preferably the distance between measurement points is small compared to the required precision of determining the distance between the resection surface and the tumour border.

3) Needle probes of 1) and 2) above in which measures have been implemented to limit the effective measurement volume of the fiber optic needle probes, such as the use of ball lenses, the use of fiber tip shaping, or by appropriate choice of fiber core diameter.

Variance in water concentration is used herein by way of example. Variance in other tissue molecular composition parameters (lipids, fats, nucleic acids, sugars, amino acids, etc.) may also be used. Different types of tumour and/or normal tissue may be better distinguished by variance in other molecular composition parameters than water, or by analysing a combination of variances in molecular composition parameters, the tumour-surrounding normal tissue showing the greater variance.

For the purpose of clarity and a concise description, features are described herein as part of the same or separate embodiments, however, it will be appreciated that the scope of the invention may include embodiments having combinations of all or some of the features described. For example, while embodiments were shown for various probes, including actuators, sensors, circuitry etcetera, also alternative ways may be envisaged by those skilled in the art having the benefit of the present disclosure for achieving a similar function and result. For example, optical, electrical, and/or mechanical components may be combined or split up into one or more alternative components. For example, while needles where shown with a bevelled angle, also needles with a straight or other formed ending can be used. Also other instruments without needles may be used. The various elements of the embodiments as discussed and shown offer certain advantages, such as providing instruments and methods for performing analysis of a depth dependent tissue composition. Of course, it is to be appreciated that any one of the above embodiments or processes may be combined with one or more other embodiments or processes to provide even further improvements in finding and matching designs and advantages. It is appreciated that this disclosure offers particular advantages to inspection of resected tissue specimens, and in general can be applied for any application wherein a tissue composition is to be analysed.

While the present systems and methods have been described in particular detail with reference to specific exemplary embodiments thereof, it should also be appreciated that numerous modifications and alternative embodiments may be devised by those having ordinary skill in the art without departing from the scope of the present disclosure. For example, embodiments wherein devices or systems are disclosed to be arranged and/or constructed for performing a specified method or function inherently disclose the method or function as such and/or in combination with other disclosed embodiments of methods or systems. Furthermore, embodiments of methods are considered to inherently disclose their implementation in respective hardware, where possible, in combination with other disclosed embodiments of methods or systems. Furthermore, methods that can be embodied as program instructions, e.g. on a non-transient computer-readable storage medium, are considered inherently disclosed as such embodiment.

Finally, the above-discussion is intended to be merely illustrative of the present systems and/or methods and should not be construed as limiting the appended claims to any particular embodiment or group of embodiments. The specification and drawings are accordingly to be regarded in an illustrative manner and are not intended to limit the scope of the appended claims. In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. In particular, all working combinations of the claims are considered inherently disclosed.

The invention claimed is:

1. A method of analysing a resected tissue sample containing tumour tissue, the method comprising
   a procedure of
      measuring localized concentrations of an analyte at a plurality of spaced apart locations around a controlled depth below a surface of the tissue sample, and
      calculating a spatial variance of the analyte based on the plurality of measured concentrations around the controlled depth;
   repeating the procedure while varying the controlled depth to obtain the spatial variance as a function of the controlled depth; and
   determining a resection margin of healthy tissue around the tumour tissue based on a section distance between a tissue surface and a depth below the tissue surface where the measured spatial variance crosses a predetermined threshold variance.

2. The method according to claim 1, comprising calculating a mean concentration of the analyte as a function of the depth; and calculating a section distance between a tissue surface and a depth below the tissue surface where either one or both the measured mean concentration or spatial variance crosses a respective or combined predetermined threshold.

3. The method according to claim 1, wherein an evaluation parameter is calculated based on a threshold for the spatial variance of the concentration of the analyte, wherein tissue at a particular depth is evaluated as tumour tissue when the spatial variance is below the threshold.

4. The method according to claim 1, wherein a combined threshold is set for a ratio between a mean concentration and a spatial variance of the analyte at a particular depth, wherein the tissue at the particular depth is classified as tumour or healthy tissue based on a comparison with the combined threshold.

5. The method according to claim 1, comprising providing a feedback signal based on a comparison between a calculated section distance and a pre-set minimum section margin.

6. The method according to claim 1, wherein the plurality of locations for calculation of the spatial variance are spaced apart along a depth direction.

7. The method according to claim 1, wherein the plurality of locations for calculation of the spatial variance are spaced apart along a lateral direction transverse to a coordinate of the controlled depth.

8. The method according to claim 1, wherein the measuring is performed using a needle comprising an optical waveguide, wherein probe light is transmitted via the optical waveguide through the needle at a controlled variable depth of the needle into a tissue surface and an optical response of the tissue sample to the probe light is measured for calculating the concentration of the analyte at the controlled variable depth.

9. An instrument for determining a resection margin of healthy tissue around tumour tissue in a resected tissue sample, the instrument comprising
  a probe configured to set a variable controlled measuring depth below a surface of the tissue sample to measure a localized concentration of an analyte at a plurality of spaced apart locations around the controlled depth; and
  a controller configured to calculate a spatial variance of the concentration of the analyte as a function of the controlled depth and determining a section distance between the tissue surface and a depth below the tissue surface where the measured spatial variance crosses a predetermined threshold variance.

10. The instrument according to claim 9, wherein the probe comprises
  a needle having a needle tip formed to penetrate a tissue surface and an optical waveguide arranged to transmit light through the needle; and
  a probe housing for holding the needle and comprising at least one of an actuator or a sensor configured to receive or generate a depth signal to determine a depth position of the needle tip relative to the tissue surface.

11. The instrument according to claim 9, wherein the optical waveguide comprises adjacent optical fibres configured to provide individual measurements of the concentration of analyte at spaced apart locations in the tissue sample.

12. The instrument according to claim 9, wherein the optical waveguide comprises a lens inside the needle, wherein the lens is configured to image light from a fibre bundle at spaced apart locations in the tissue sample.

13. The instrument according to claim 9, wherein the lens comprises a gradient index lens.

14. A non-transitory computer readable medium with software instructions that when executed by an instrument causes execution of a method of analysing a resected tissue sample containing tumour tissue, the method comprising a procedure of measuring localized concentrations of an analyte at a plurality of spaced apart locations around a controlled depth below a surface of a tissue sample, and calculating a spatial variance of an analyte based on the plurality of measured concentrations around the controlled depth; repeating the procedure while varying the controlled depth to obtain the spatial variance as a function of the controlled depth; and determining a resection margin of healthy tissue around the tumour tissue based on a section distance between the tissue surface and a depth below the tissue surface where the measured spatial variance crosses a predetermined threshold variance.

* * * * *